(12) United States Patent
Takigawa et al.

(10) Patent No.: US 8,399,466 B2
(45) Date of Patent: *Mar. 19, 2013

(54) COMPOSITION FOR REGENERATIVE TREATMENT OF CARTILAGE DISEASE

(75) Inventors: Masaharu Takigawa, Okayama (JP);
Naoki Sakurai, Solana-Beach, CA (US);
Toshiki Takagi, Itami (JP); Noriyuki Yanaka, Higashihiroshima (JP); Yuji Horikiri, Kawanishi (JP); Takashi Tamura, Amagasaki (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 88 days.

This patent is subject to a terminal disclaimer.

(21) Appl. No.: 12/782,514

(22) Filed: May 18, 2010

(65) Prior Publication Data

US 2010/0226993 A1 Sep. 9, 2010

Related U.S. Application Data

(62) Division of application No. 11/707,008, filed on Feb. 16, 2007, which is a division of application No. 10/478,432, filed as application No. PCT/JP02/04930 on May 22, 2002, now abandoned.

(30) Foreign Application Priority Data

May 23, 2001 (JP) ................................ 2001-154048

(51) Int. Cl.
*A61K 31/495* (2006.01)
*A61K 31/435* (2006.01)
*A61K 31/38* (2006.01)

(52) U.S. Cl. .................... 514/248; 514/277; 514/438

(58) Field of Classification Search .............. 514/277, 514/438, 248
See application file for complete search history.

(56) References Cited

U.S. PATENT DOCUMENTS

| | | | |
|---|---|---|---|
| 4,193,926 A | 3/1980 | Horowski et al. |
| 4,542,025 A | 9/1985 | Tice et al. |
| 5,000,886 A | 3/1991 | Lawter et al. |
| 5,171,217 A | 12/1992 | March et al. |
| 5,223,504 A | 6/1993 | Noverola et al. |
| 5,288,496 A | 2/1994 | Lewis et al. |
| 5,294,446 A | 3/1994 | Schlameus et al. |
| 5,503,851 A | 4/1996 | Mank et al. |
| 5,552,438 A | 9/1996 | Christensen, IV |
| 5,605,914 A | 2/1997 | Muller |
| 5,614,515 A | 3/1997 | Rodgers et al. |
| 5,804,588 A | 9/1998 | Dyke et al. |
| 5,910,492 A | 6/1999 | Hoshino et al. |
| 5,922,253 A | 7/1999 | Herbert et al. |
| 5,939,388 A | 8/1999 | Rosen et al. |
| 6,010,711 A | 1/2000 | O'Keefe et al. |
| 6,011,060 A | 1/2000 | Laurent et al. |
| 6,197,326 B1 | 3/2001 | Suzuki et al. |
| 6,214,008 B1 | 4/2001 | Illi |
| 6,348,602 B1 | 2/2002 | Fowler et al. |
| 6,451,335 B1 | 9/2002 | Goldenheim et al. |
| 6,458,829 B1 | 10/2002 | Shen et al. |
| 2002/0123520 A1 | 9/2002 | Marfat et al. |
| 2004/0180900 A1 | 9/2004 | Takigawa et al. |
| 2007/0155652 A1 | 7/2007 | Takigawa et al. |

FOREIGN PATENT DOCUMENTS

| | | |
|---|---|---|
| CA | 2 278 217 | 11/1998 |
| DE | 100 61 137 | 6/2002 |
| EP | 0 158 380 A1 | 10/1985 |
| EP | 0 163 965 A2 | 12/1985 |
| EP | 0 251 476 | 1/1988 |
| EP | 0 260 817 A1 | 3/1988 |
| EP | 0 403 383 B1 | 12/1990 |
| EP | 0 459 505 A1 | 4/1991 |
| EP | 0 432 856 A2 | 6/1991 |
| EP | 0 497 564 B1 | 1/1992 |
| EP | 0 557 016 A1 | 8/1993 |
| EP | 0 623 607 A1 | 11/1994 |
| EP | 0 738 715 A2 | 10/1996 |
| EP | 0 748 805 A1 | 12/1996 |
| EP | 0 781 548 | 7/1997 |
| EP | 0 848 000 A1 | 6/1998 |
| EP | 0 911 025 A1 | 4/1999 |
| EP | 1 053 746 | 11/2000 |
| EP | 1 308 440 A1 | 5/2003 |
| JP | 56-19324 | 5/1981 |
| JP | 60-67417 | 4/1985 |
| JP | 60-100516 | 6/1985 |
| JP | 62-201816 | 9/1987 |
| JP | 63-091325 | 4/1988 |
| JP | 1-155942 | 6/1989 |
| JP | 01-305929 | 12/1989 |
| JP | 4-364179 | 12/1992 |
| JP | 5-58882 | 3/1993 |
| JP | 5-70363 | 3/1993 |
| JP | 5-194200 | 8/1993 |
| JP | 5-229987 | 9/1993 |
| JP | 6-32732 | 2/1994 |
| JP | 6-211648 | 8/1994 |

(Continued)

OTHER PUBLICATIONS

Peters et al. http://www.hughston.com 3 pages (2001), 3 pages.*
European Office Action issued in Application No. 02 771 771.9-1216 on Aug. 24, 2010, 8 pages.
Dyke H.J. et al., "The Therapeutic Potential of PDE4 inhibitors," Expert Opinion on Investigational Drugs, Ashely Publications Ltd., London, GB, vol. 8, No. 9, 1999, pp. 1301-1325.
Kossetsu Chiryougaku (Fracture Therapeutics), Apr. 2000, pp. 29-37, 46-51, Nanko-do-P2 with English translation.

(Continued)

Primary Examiner — Shirley V Gembeh
(74) Attorney, Agent, or Firm — Finnegan, Henderson, Farabow, Garrett & Dunner, L.L.P.

(57) ABSTRACT

A composition for regenerative treatment of cartilage disease, which comprises a PDE4 inhibitor as an active ingredient, specifically a composition comprising a PDE4 inhibitor and a biocompatible and biodegradable polymer is provided, which composition, when formulated into a form suited to administer locally to affected cartilage region, such as microsphere preparation, can provide a pharmaceutical composition showing an excellent effect in regenerative treatment of cartilage.

20 Claims, 9 Drawing Sheets

FOREIGN PATENT DOCUMENTS

| | | |
|---|---|---|
| JP | 6-305983 | 11/1994 |
| JP | 07 101861 | 8/1995 |
| JP | 8-151321 | 6/1996 |
| JP | 9-59255 | 3/1997 |
| JP | 9-110678 | 4/1997 |
| JP | 09-169665 | 6/1997 |
| JP | 9-221417 | 8/1997 |
| JP | 9-221418 | 8/1997 |
| JP | 9-263545 | 10/1997 |
| JP | 10-158267 | 6/1998 |
| JP | 10-182499 | 7/1998 |
| JP | 10-226685 | 8/1998 |
| JP | 2001-187749 | 7/2001 |
| JP | 2001-198208 | 7/2001 |
| WO | WO 90/09783 | 9/1990 |
| WO | WO 91/01720 | 2/1991 |
| WO | WO 91/16314 | 10/1991 |
| WO | WO 92/12961 | 8/1992 |
| WO | WO 92/15282 | 9/1992 |
| WO | WO 93/09118 | 5/1993 |
| WO | WO 94/02455 | 2/1994 |
| WO | WO 94/22852 | 10/1994 |
| WO | WO 94/25437 | 11/1994 |
| WO | WO 95/00516 | 1/1995 |
| WO | WO 95/04045 | 2/1995 |
| WO | WO 95/08534 | 3/1995 |
| WO | WO 95/14667 | 6/1995 |
| WO | WO 95/14681 | 6/1995 |
| WO | WO 95/20578 | 8/1995 |
| WO | WO 95/35282 | 12/1995 |
| WO | WO 96/00215 | 1/1996 |
| WO | WO 96/00218 | 1/1996 |
| WO | WO 96/06843 | 3/1996 |
| WO | WO 96/20698 | 7/1996 |
| WO | WO 96/28143 | 9/1996 |
| WO | WO 96/31485 | 10/1996 |
| WO | WO 97/13502 | 4/1997 |
| WO | WO 97/18208 | 5/1997 |
| WO | WO 97/22585 | 6/1997 |
| WO | WO 97/22586 | 6/1997 |
| WO | WO 97/23457 | 7/1997 |
| WO | WO 97/29750 | 8/1997 |
| WO | WO 97/40032 | 10/1997 |
| WO | WO 97/44036 | 11/1997 |
| WO | WO 97/44322 | 11/1997 |
| WO | WO 98/02440 | 1/1998 |
| WO | WO 98/09961 | 3/1998 |
| WO | WO 98/11113 | 3/1998 |
| WO | WO 98/13348 | 4/1998 |
| WO | WO 98/14432 | 4/1998 |
| WO | WO 98/18796 | 5/1998 |
| WO | WO 98/31674 | 7/1998 |
| WO | WO 98/56431 | 12/1998 |
| WO | WO 99/23076 | 5/1999 |
| WO | WO 99/47186 | 9/1999 |
| WO | WO 99/50270 | 10/1999 |
| WO | WO 99/65474 | 12/1999 |
| WO | WO 00/50011 | 8/2000 |
| WO | WO 00/55112 | 9/2000 |
| WO | WO 00/66584 | 11/2000 |
| WO | WO 01/13953 | 3/2001 |
| WO | WO 01/45705 A1 | 6/2001 |
| WO | WO 01/46136 | 6/2001 |
| WO | WO 01/57025 | 8/2001 |
| WO | WO 01/76575 A2 | 10/2001 |
| WO | WO 01/93909 | 12/2001 |
| WO | WO 02/14280 | 2/2002 |
| WO | WO 02/050875 | 8/2002 |
| WO | WO 02/060898 | 8/2002 |

OTHER PUBLICATIONS

Proc Natl. Acad. Sci. USA vol. 87, p. 2220-2224 (1990).
Trends in Pharmacological Sciences, Vo. 11. p. 150-155 (1990).
Advances in Cyclic Nucleotide Research vol. 10, p. 69-92 (1979).
Cellular Signaling vol. 9, Issues 3-4, p. 227-236 (1997).
Journal of Controlled Release 59 p. 77-86 (1999).
Journal of Controlled Release 33 p. 237-243 (1995).
Biomaterials vol. 21 p. 2405-2412 (2000).
International Journal of Pharmaceutics vol. 206 p. 1-12 (2000).
Drug Development and Industrial Pharmacy vol. 24(8) p. 703-727 (1998).
European J. Pharm. Biopharm. vol. 42(1) p. 16-24 (1996).
Spray Drying Handbook (1984).
Microcapsulation and Related Drug Processes (1984).
International Journal of Pharmaceutics vol. 187, p. 143-152 (1999).
J. Jpn. Orthop. Assoc. 74(6) 2000 S-1737, S-1735, S-1330, S-1814 with English translations.
J. Jpn. Orthop. Assoc 73(8) 199 S-1519 with English translations.
Exp. Toxicol. Pathol 45(8) 473-479 (1993/94).
Journal of Bone and Mineral Metabolisum vol. 17(2) 202 (1999) with English translation.
J. Bone and Mineral Res. 14 (Suppl. 1) S349 (1999).
J. Bone and Mineral Res. 14 (Suppl. 1) S354 (1999).
J. Bone and Mineral Res. 14 (Suppl. 1) S504 (1999).
Francischi et al., "Anti-inflammatory and analgesic effects of the phosphodiesterase 4 inhibitor rolipram in a rat model of arthritis," European Journal of Pharmacology, 399 (2000) 243-249.
Hitoshi Sezaki, "Drug Delivery System," Nankodo Co., Ltd. 1986, 185-189 w/trans. p. 185-line 11 to p. 187-line 12.
Tenor, Hermann et al., Phosphodiesterase isoenzyme familes in human osteoarthritis chondrocytes-functional importance of phosphodiesterase 4, British Journal of Pharmacology, 2002, vol. 135, No. 3 pp. 609-618.
U.S. Appl. No. 10/478,709, filed Nov. 24, 2003.
"Development of research on polylactic acid and polylactic-co-glycolic acid microspheres." Journal of China Pharmaceutical University 1999, vol. 30, No. 1, pp. 73-77. (w/English translation).
Norman, "PDE4 Inhibitors 1998," Expert Opinion on Therapeutic Patents, United Kingdom, vol. 8, No. 7, 1998, pp. 771-784.
Chambers et al., "Biarylcarboxamide inhibitors of phosphodiesterase IV and tumor necrosis factor-alpha," Bioorganic and Medicinal Chemistry Letters, vol. 7, No. 6, 1997, pp. 739-744.
Lamprecht et al., "Design of rolipram-loaded nanoparticles: comparison of two preparation methods," Journal of Controlled Release, vol. 71, No. 3, Apr. 2001, pp. 297-306.
Lamprecht et al., "Biodegradable nanoparticles for targeted drug delivery in treatment of inflammatory bowel disease," Journal of Pharmacology and Experimental Therapeutics, vol. 299, No. 2, 2001, pp. 775-781.
Supplementary Partial European Search Report issued in European Application No. 02 77 1771.9-2107, Dec. 12, 2006, 30 pages.
International Search Report, PCT/JP02/04930, Aug. 27, 2002.
Communication from European Patent Office in EP Application 02 771 771.9, May 8, 2007, 4 pages.
Miyamoto et al., "Reduction of Bone Loss by Denbutylline, an Inhibitor of Phosphodiesterase 4," Biochemical Pharmacology, vol. 54, pp. 613-617, 1997.
Communication from European Patent Office in EP Application 02 771 772.7, May 16, 2007, 5 pages.
Shapiro et al., "Cell origin and differentiation in the repair of full-thickness defects of articular cartilage," Journal of Bone and Joint Surgery, Series A, vol. 75(4), pp. 532-553, 1993.
Shohei Kasugai et al., "Potential of PDE4 Inhibitors in the Treatment of Osteopenia," Drug News Perspect 12(9), Nov. 1999.
Shohei Kasugai et al., "Anabolic effect of a phosphodiesterase 4 (PDE4) inhibitor in bone and its possible mechanism," Jpn. J. of Pharmacol 79, Suppl. 1, 277 (1999).
Yoshihiro Waki et al., "Effects of XT-44, a Phosphodiesterase 4 Inhibitor, in Osteoblastgenesis and Osteoclastgenesis in Culture and Its Therapeutic Effects in Rat Osteopenia Models," Jpn. J. Pharmacol. 79, 477-483 (1999).
T. Kinoshita, "Phosphodiesterase Inhibitors, Pentoxifylline and Rolipram, Increase Bone Mass Mainly by Promoting Bone Formation in Normal Mice,"Bone, vol. 27, No. 6 (Dec. 2000) 811-817.
H. Horiuchi et al., "Enhancement of Bone Morphogenetic Protein-2-Induced New Bone Formation in Mice by the Phosphodiesterase Inhibitor Pentoxifylline," Bone vol. 28, No. 3, Mar. 2001, pp. 290-294, XP-002389298.

Kasugai et al., "Phosphodiesterase IV Inhibitor (Rolipram) Stimulates Osteoblastic Differentiation in Rat Bone Marrow Cell Culture," Japanese J. of Pharma., J. Pharma. Soc., vol. 73, No. Supp. 1, 1997, pp. 289P, AbstractP-685.

H. Horiuchi et al., "Effect of Phosphodiesterase Inhibitor-4, Rolipram, on New Bone Formations by Recombinant Human Bone Morphogenetic Protein-2," Bone vol. 30, No. 4, Apr. 2002, pp. 589-593, XP-002389299.

Igaku Daijiten, 18th Ed., published by Nanzando, pp. 719-720-P1, 1998.

Shohei Kasugai et al., "Potential of PDE4 Inhibitors in the Treatment of Osteopenia," Drug News Perspect 12(9), pp. 529-534, 1999.

Kaminuma et al., "A selective type 4 phosphodiesterase inhibitor, T-440, modulates intracellular cyclic AMP level and interleukin-2 production of Jurkat cells," Immunopharmacology, vol. 38, No. 3, p. 247-252, 1998.

Japanese Office Action issued in Application No. 2002-591036 on May 7, 2008, 3 pages.

Bohatiruk F.P., Am. J. Anat., 126 (1969) 243-254.

Igaku-Daijiten, 18th Ed., published by Nanzando, pp. 719-720-P1, 1998.

* cited by examiner

Fig. 2
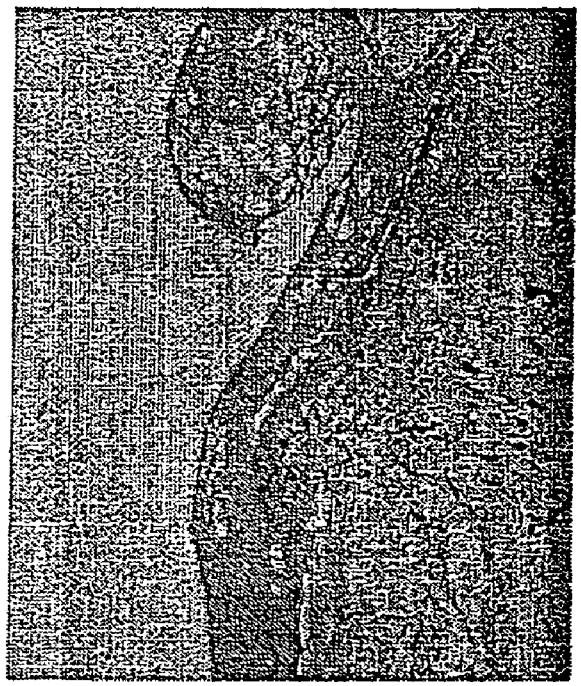
Compound (1)-contaning Microphere (Example 2)
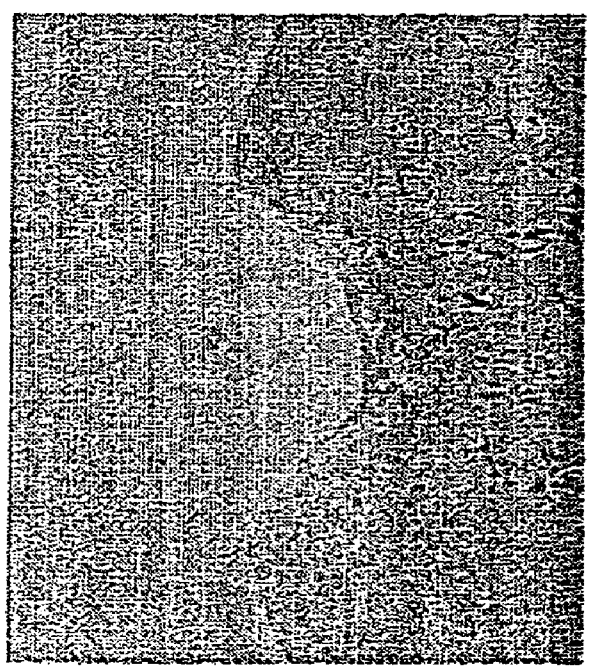
Mirosphere of Control Example 1

COMPOSITION FOR REGENERATIVE TREATMENT OF CARTILAGE DISEASE

This is a divisional of application Ser. No. 11/707,008, filed Feb. 16, 2007, which is a divisional of application Ser. No. 10/478,432, filed Nov. 21, 2003, now abandoned, which is a §371 of PCT/JP02/04930, filed May 22, 2002, all of which are incorporated herein by reference.

TECHNICAL FIELD

The present invention relates to a composition for regenerative treatment of cartilage disease, specifically, to a pharmaceutical composition for regenerative treatment of cartilage disease such as osteoarthrosis (degenerative joint disease), chondrodystrophy, degenerative discopathy or meniscus injury.

BACKGROUND ART

Cartilage is considerably elastic that plays a role in the construction of skeleton together with bone and the protection of internal organs. Cartilage tissue consists of chondrocytes and cartilage matrix surrounding the same.

Cartilage is formed by mesenchyme-originated chondroblasts which cells produce matrix in circumference in the process of cell division and growth. The cartilage matrix consists of amorphous matrix and fibrous components, and is classified into the following groups according to the ratio of components: (1) hyaline cartilage (articular cartilage, costicartilage, thyroid cartilage etc.); (2) fibrocartilage (discus intervertebrali, pubic symphysis etc.); and (3) elastic cartilage (pharynx lid cartilage, cartilage of acoustic meatus, auricular cartilage, etc.) IGAKU-DAIJITEN, 18th edition, published by Nanzando, pp. 1542.

The main components of cartilage matrix are proteoglycan and collagen (Type II, Type IX and the like). It is known that proteoglycan participates in the imbibition (swelling) nature peculiar to cartilage tissue, and collagen in the rigidity of cartilage against the tension and shearing force.

In proteoglycan of cartilage matrix, it is considered that glucosaminoglycans such as chondroitin sulfate, keratan sulfate are connected with a core protein of about 220,000 molecular weight to form macromolecules, wherein glucosaminoglycans hydrates many water molecules, which contributes to the imbibition nature of cartilage. The Bone, Vol. 4, pp. 8 (1994).

Articular cartilage has a calcification layer at the transmigration region with bone tissue, and, after the completion of growth, nutrients are supplied to chondrocytes from synovial fluid, and are hardly supplied directly from blood. In addition, articular cartilage is formed from hyaline cartilage of high cell differentiation degree, and hence is a sensitive organ with extremely low regenerative ability.

The surface of articular cartilage is covered by highly viscous synovial fluid, and by virtue of lubrication mechanism of lubricant comprising as a principal component hyaluronic acid-protein complex, the smooth joint kinematics is maintained. However, it is considered that there is so-called durability in articular cartilage, and alteration of joints with aging is unavoidable physiological phenomenon.

Examples of known, diseases caused by cartilage disorder include osteoarthrosis, chondrodystrophy, degenerative discopathy or meniscus injury.

Among them, osteoarthrosis is a disease wherein a proliferative change of bone and articular cartilage occurs on the basis of a regressive change of tissue constituting a joint, mainly, articular cartilage, finally leading to a remarkable morphological change of the joint, which disease has markedly increased with the aging of population. In particular, the knee joint anthropathy can prevent patients from maintaining the standing position or walking normally as the pathology progresses, and lead to the significant decrease of their ADL (Ability of Daily Life) which possibly results in a bedridden condition.

Treatment of osteoarthrosis can be classified mainly into conservative treatment and surgical therapy. Conservative treatment is carried out by the following methods, for example, (1) administration of non-steroidal antiinflammatory analgesic; (2) thermotherapy; (3) control of weight; (4) therapy with braces; (5) infra-articular infusion of steroidal antiinflammatory analgesic; (6) intra-articular infusion of hyaluronate formulation. In cases wherein conservative treatment is ineffective, or the disease is in progressed or terminal stage, surgical therapy is conducted by (a) arthroscopic irrigation surgery; (b) high tibial osteotomy or (c) artificial joint replacement, and the like. Senility and Disorder, Vol. 10, 2nd. issue, pp. 61-69, (1997) & 6th issue, pp. 66-77 (1997).

There are various compounds having PDE4 inhibitory activity, which can suppress the release of inflammatory mediator by inhibiting the PDE4 activity. J. Mol. Cell. Cardiol., 12 (Suppl.II), S61 (1989).

It is described that a compound having PDE4 inhibitory activity suppresses the production of TNF-α which is a cytokine released from mononuclear phagocytes in response to immunostimulants, and is useful in treatment of various inflammatory diseases caused by TNF-α. JP 2000-503678A, JP 2000-502724A, JP 2000-510105A, JP 2000-514804A, 2000-502350A, JP 2000-501741A, and the like.

However, it has not been known that PDE4 inhibitor is effective for reparative treatment of cartilage diseases at all.

DISCLOSURE OF INVENTION

As stated above, cartilage is known to have extremely low regenerative ability, and it was considered that, once damaged, the regeneration thereof is almost impossible. The conventional pharmacotherapy was only conservative treatment which restrains the progressing of disorder. Accordingly, it has long been demanded the development of pharmacotherapy and/or pharmaceutical agent that enables to conduct regenerative treatment of cartilage diseases.

The present inventors have first found that PDE4 is produced by chondrocytes and then compounds having PDE4 inhibitory activity show activity on cartilage diseases. The inventors have intensively studied and found that the said PDE4 inhibitors are useful in regenerative treatment of cartilage diseases, and established the present invention.

The present invention provides a composition for regenerative treatment of cartilage disease, which comprises a PDE4 inhibitor as an active ingredient. In particular, the present invention provides a pharmaceutical preparation suited to administer locally to the site of cartilage disease, specifically, a composition for regenerative treatment of cartilage disease in the form of microsphere preparation.

BRIEF DESCRIPTION OF DRAWINGS

FIG. 2 is a copy of microphotograph showing the results of observation under microscope of regeneration of old rabbit articular cartilage in the presence of microsphere containing Compound (1) or free of Compound (1).

BEST MODE FOR CARRYING OUT THE INVENTION

Figure 1:
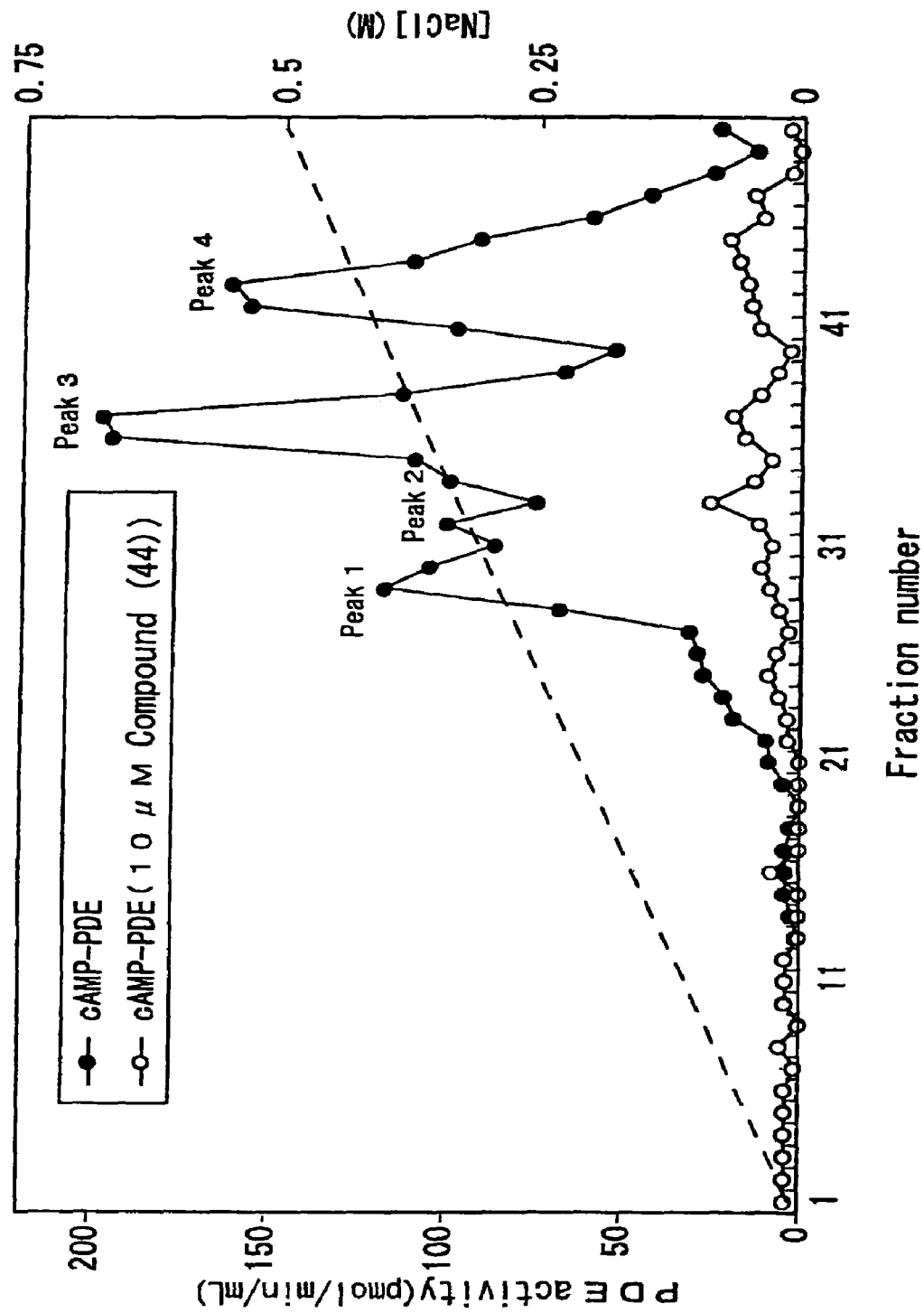
FIG. 1 is a graph showing the cAMP hydrolyzing activity in each fraction obtained by fractionating rabbit articular chondrocyte extract by Mono Q Sepharose column chromatography, in the presence of Compound (44) (○) and absence of Compound (44) (●).

The composition of the present invention for regenerative treatment of cartilage disease can enhance the expression of cartilage matrix protein encoding gene and thereby showing superior matrix production promoting effect on cartilage especially on articular cartilage that has extremely low regenerative activity, and cure cartilage diseases through the regeneration of cartilage.

As herein used, the term "regenerative treatment of cartilage disease" refers to treatment not only for arresting the progress of cartilage disease but also for restoring a cartilage undergone deformation and/or detrition due to illness, lesion, or the like to the original state.

The pharmaceutical composition of the present invention can be prepared by combining a PDE4 inhibitor as an active ingredient and a conventional pharmaceutically acceptable excipient or a diluting agent therefor. Preferred pharmaceutical composition is a sustained release composition for local administration, which contains a PDE4 inhibitor(s) and a biocompatible and biodegradable polymer(s). The composition for local administration is preferably in the form of depot formulation, and more preferably in the form of microsphere, which microsphere can be formulated as an injectable preparation.

Examples of PDE4 inhibitor usable as an active ingredient of pharmaceutical compositions of the present invention include all the compounds having PDE4 inhibitory activity, for example, those described in JP 05-229987A (1993), JP 09-59255A (1997), JP 10-226685A (1998), EP 158380, WO/94/25437, U.S. Pat. No. 5,223,504, WO/95/4045, EP 497564, EP 569414, EP 623607, EP 163965, U.S. Pat. No. 5,605,914, WO/95/35282, WO/96/215, U.S. Pat. No. 5,804,588, U.S. Pat. No. 5,552,438, WO/93/9118, WO/96/31485, EP 459505, WO/97/22585, EP 738715, WO/91/16314, WO/96/218, WO/97/18208, EP 158380, WO/99/50270, EP 260817, WO/98/11113, WO/94/22852, EP 432856, U.S. Pat. No. 4,193,926, WO/98/13348, WO/96/6843, JP 2000-503678A (WO/98/14432), JP 2000-502724A (WO/98/9961), JP 2000-510105A (WO/97/40032), JP 2000-514804A. (WO/98/2440), JP 2000-502350A (WO/97/23457), JP 2000-501741A (WO/97/2585), and the like.

PDE can be classified into PDE1-5 according to the teaching of "Trends in Pharmacological Sciences, vol. 11, pp. 150-155", and PDE4 inhibitors suitable for the present composition for regenerative treatment of cartilage disease are preferably selective to PDE4 with higher inhibitory activity against PDE4 compared to others (PDE1-3, 5), more preferably have 10 times or more inhibitory activity on PDE4 than on the other PDEs. The inhibitory activity of such PDE4 inhibitor on PDE4 is particularly preferably 50 times or more, and yet more preferably 100 times or more of that on the other PDEs.

Preferable PDE4 inhibitors are compounds of which $IC_{50}$ of PDE4 inhibitory activity is 0.1-1000 nM, preferably 0.1-100 nM, more preferably less than 100 nM, when determined by a method described in "Advances in Cyclic Nucleotide Research", vol. 10, pp. 69-92, 1979, Raven Press.

Specific examples of selective PDE4 inhibitors include Compounds (1) to (57) represented by the following formulas or pharmaceutically acceptable salts thereof.

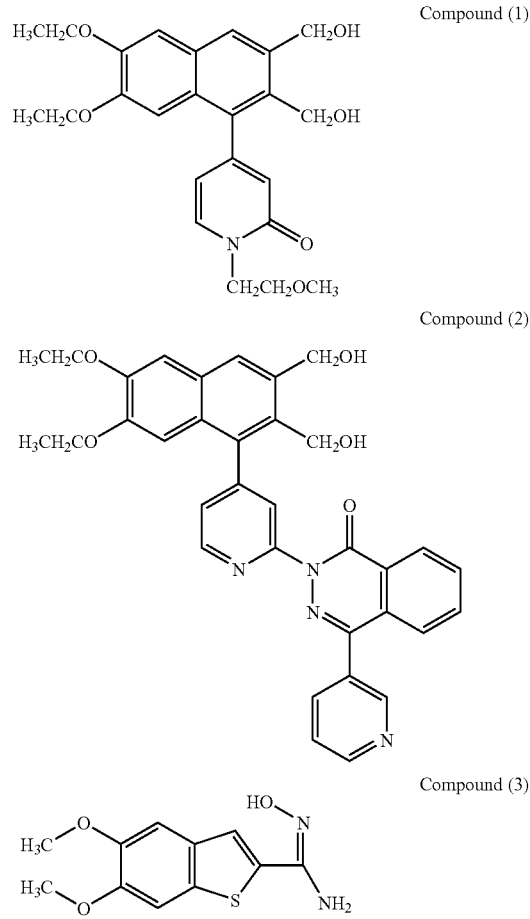

-continued
Compound (4)
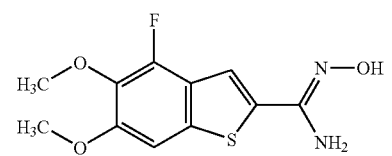
Compound (5)
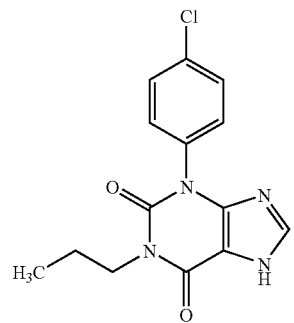
Compound (6)
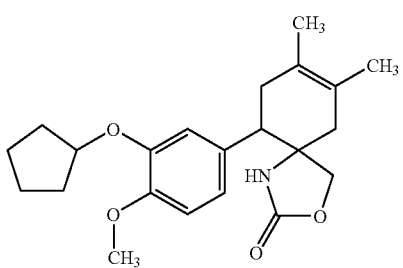
Compound (7)
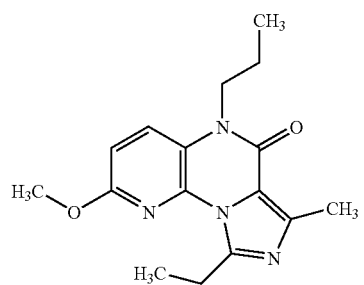
Compound (8)
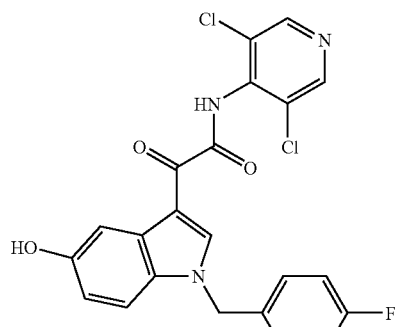
Compound (9)
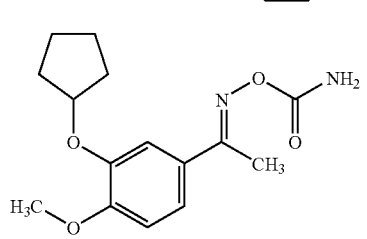
-continued
Compound (10)
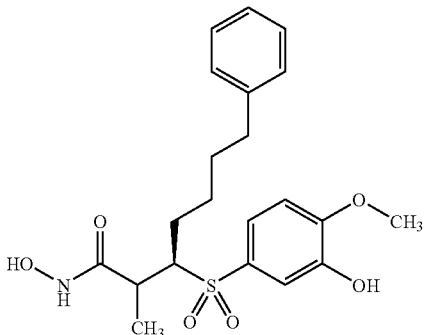
Compound (11)
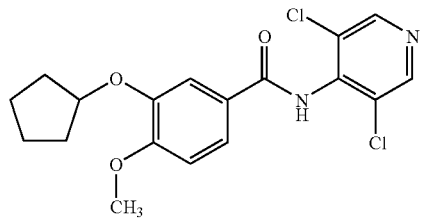
Compound (12)
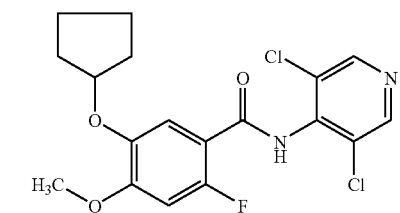
Compound (13)
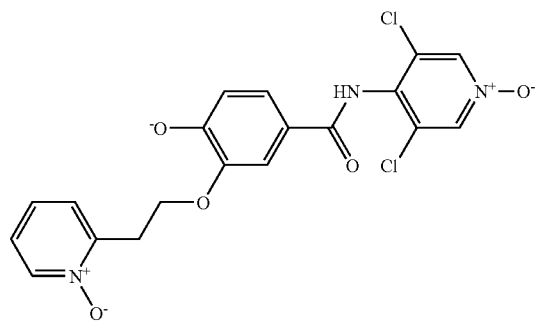
Compound (14)

Compound (15)
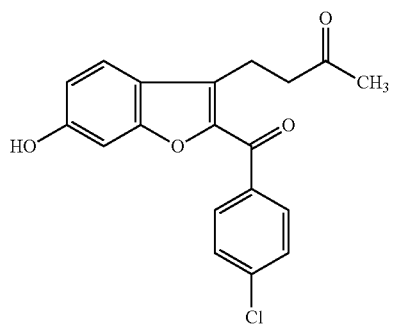
Compound (16)
Compound (17)
Compound (18)
Compound (19)
Compound (20)
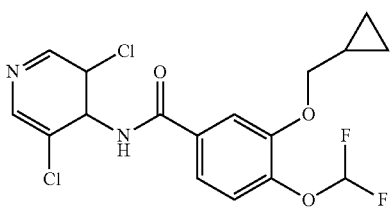
Compound (21)
Compound (22)
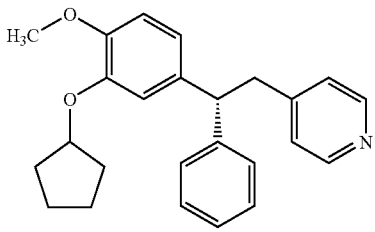
Compound (23)
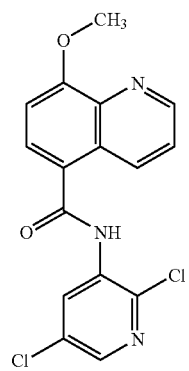
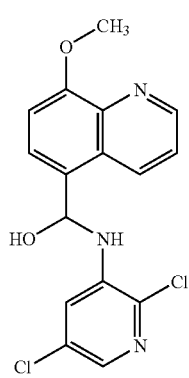
Compound (24)
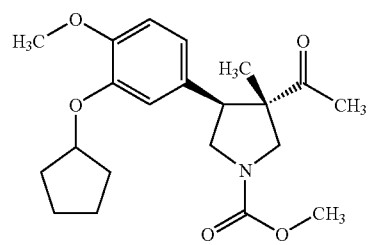

Compound (25)
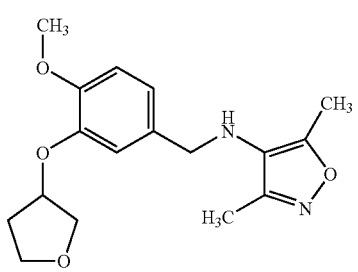
Compound (26)
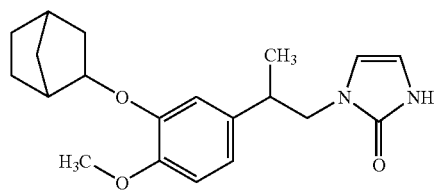
Compound (27)
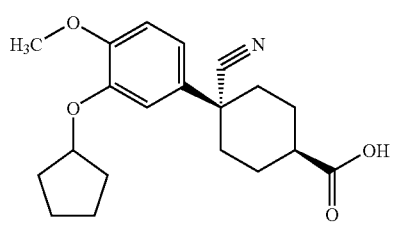
Compound (28)
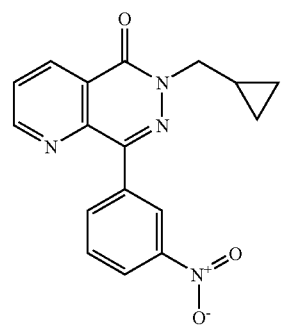
Compound (29)
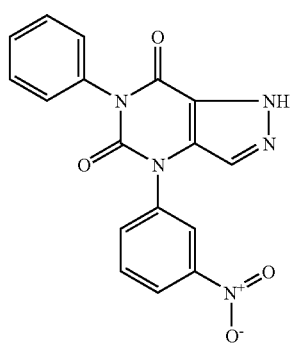
Compound (30)
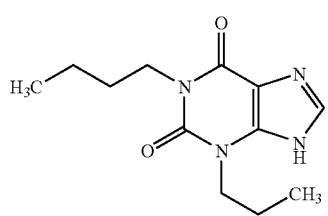
Compound (31)
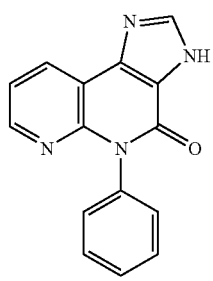
Compound (32)
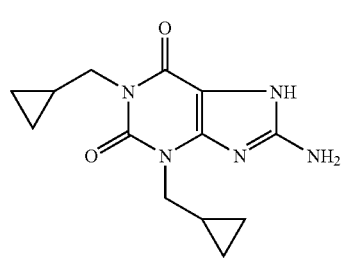
Compound (33)
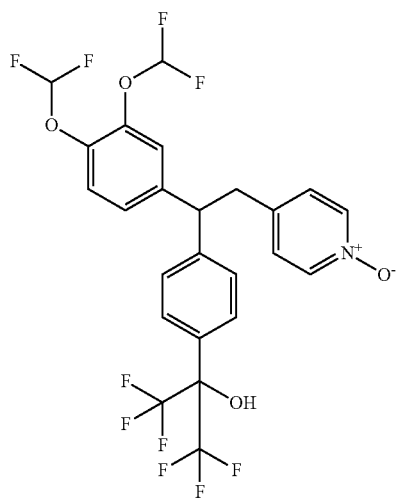
Compound (34)
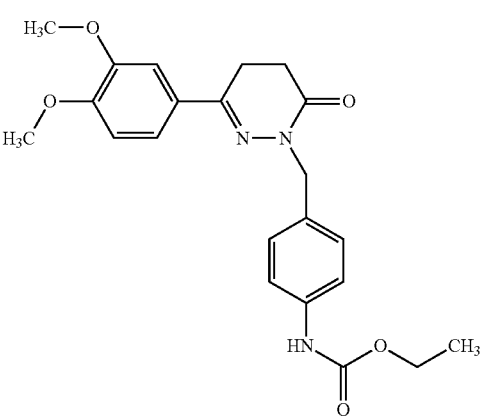

-continued
Compound (35)
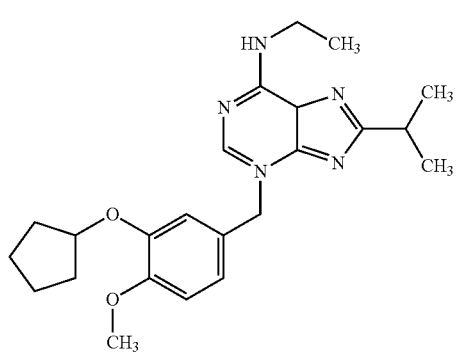
Compound (36)
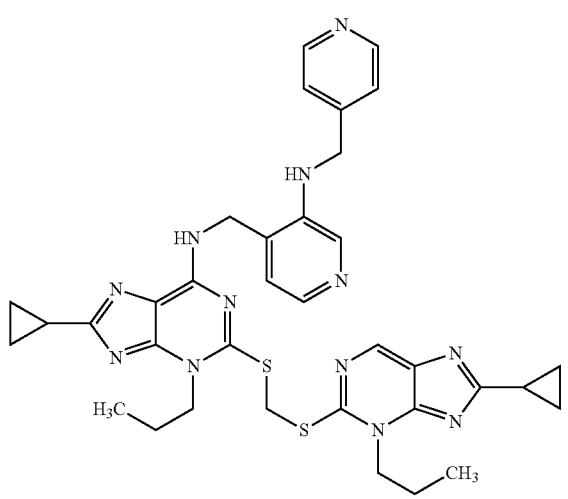
Compound (37)
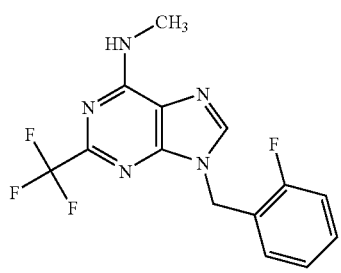
Compound (38)
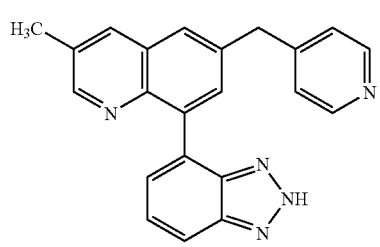
Compound (39)
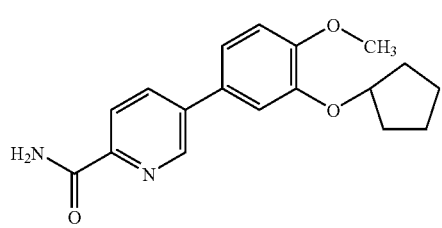
-continued
Compound (40)
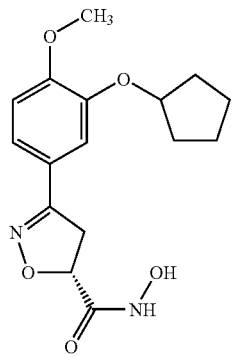
Compound (41)
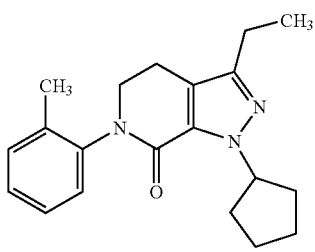
Compound (42)
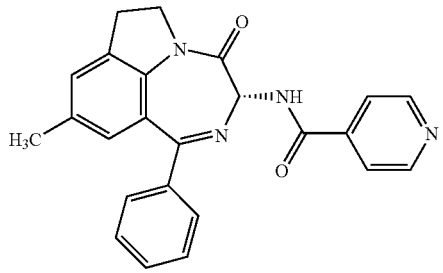
Compound (43)
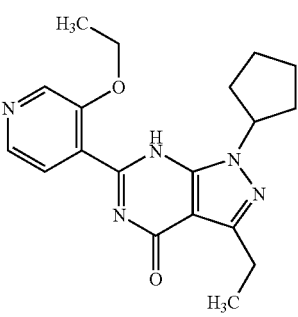
Compound (44)
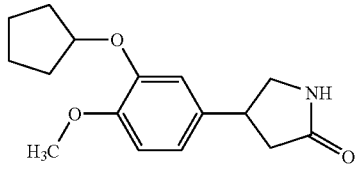

-continued
Compound (45)
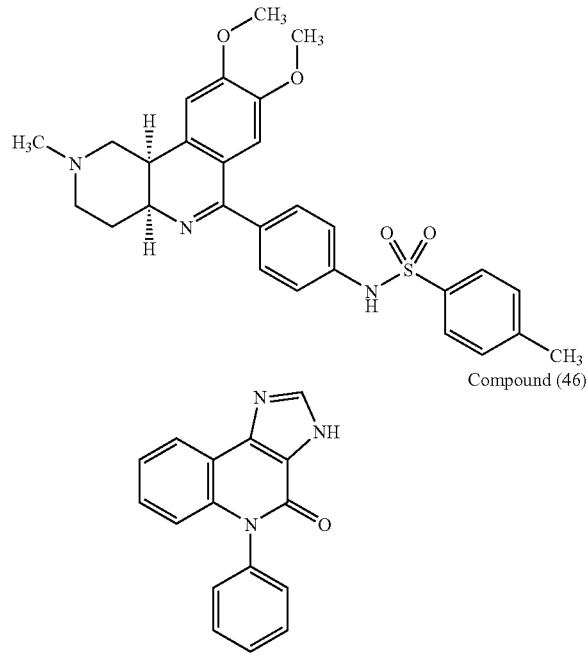
Compound (46)
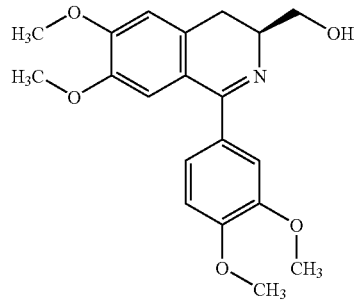
Compound (47)
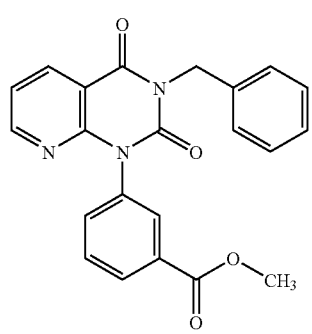
Compound (48)
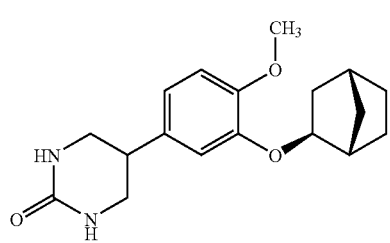
Compound (49)
-continued
Compound (50)
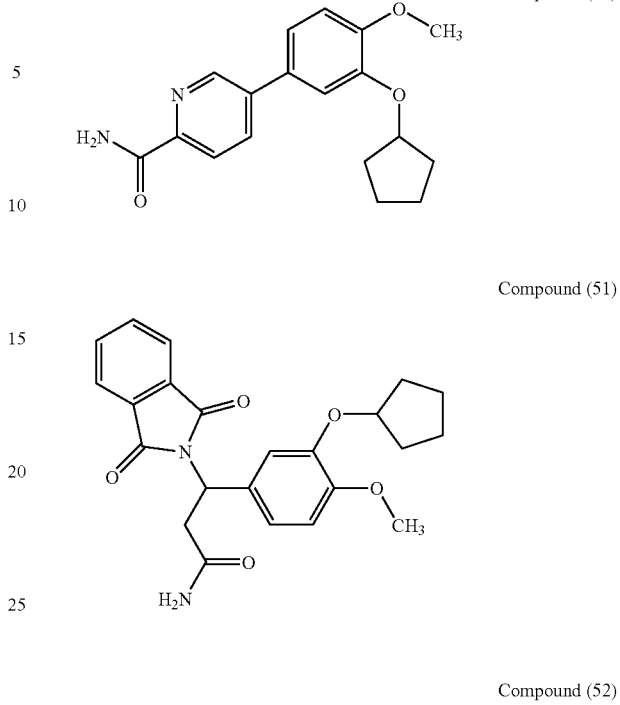
Compound (51)
Compound (52)
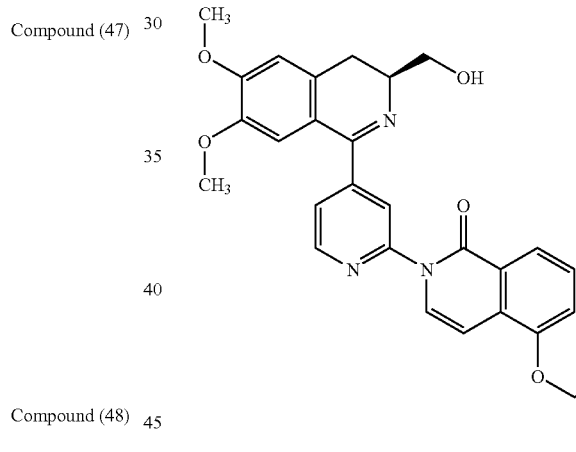
Compound (53)
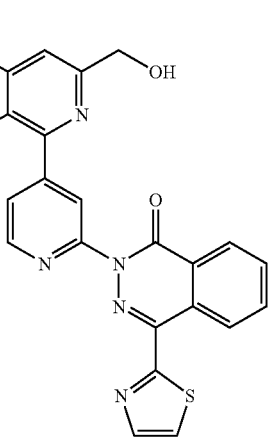

Compound (54)

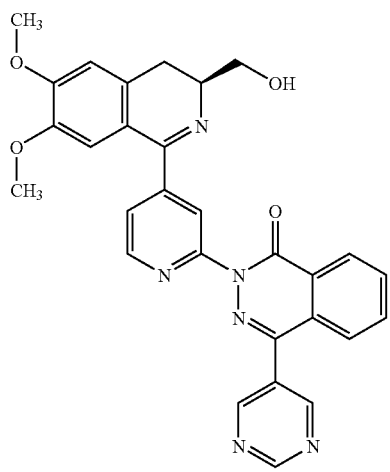

Compound (54)

Compound (57)

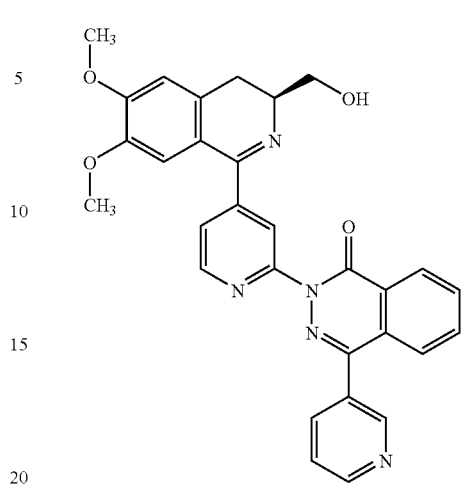

Compound (56)

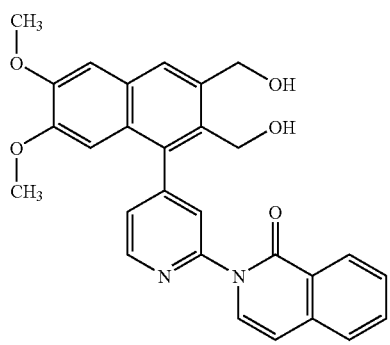

The compounds having PDE4 inhibitory activity can be classified into (A) to (D) below according to the chemical structure, and a PDE4 inhibitor for the present invention can be selected from these compounds appropriately; however, preferred compounds belong to (A) and (B), in particular, (A).

(A) Compounds having naphthalene skeleton or a partial structure analogous thereto [e.g., Compounds (1), (2), (38), (47), and (52) to (57)];

(B) Compounds having 3-cyclopentyloxy-4-methoxyphenyl structure or a partial structure analogous thereto [e.g., Compounds (6), (9), (11), (12), (14), (17), (19), (20), (21), (24), (25), (26), (27), (33), (34), (35), (39), (40), (44), (49), (50) and (51)];

(C) Compounds having a xanthine skeleton or a partial structure analogous thereto [e.g., Compounds (5), (7), (28), (29), (30), (31), (32), (36), (37), (41), (43) and (46)]; and (D) Compounds having a different structure from those described in (A) to (C) above [e.g., Compounds (3), (4), (8), (10), (13), (15), (16), (18), (22), (23), (42), (45) and (48)].

Examples of compounds of group (A) include those shown by the following formulas (I) to (III) and pharmacologically acceptable salts thereof.

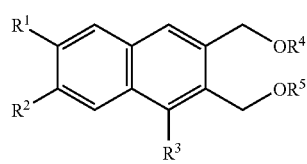

(I)

Wherein $R^1$ and $R^2$ are the same or different and each a hydrogen atom, a hydroxyl group, a cyclo-lower alkyloxy group, or an optionally substituted lower alkoxy group, or bind together at the ends to form a lower alkylenedioxy group;

$R^3$ is an optionally substituted 6-membered nitrogen-containing heterocyclic group; and $-OR^4$ and $-OR^5$ are the same or different and each an optionally protected hydroxyl group. JP 05-229967A, (1993).

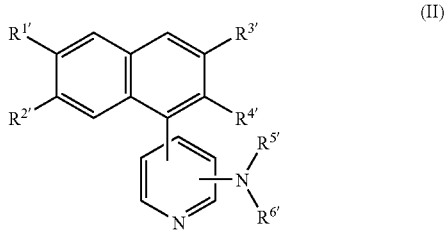

(II)

Wherein $R^{1'}$ and $R^{2'}$ are the same or different and each a hydrogen atom or an optionally protected hydroxyl group; either of $R^{3'}$ and $R^{4'}$ is an optionally protected hydroxy-substituted methyl group and the other is a hydrogen atom, a lower alkyl group or an optionally protected hydroxy-substituted methyl group; and $R^{5'}$ and $R^{6'}$ are the same or different and each a hydrogen atom, an optionally substituted lower alkyl group, an optionally substituted phenyl group or an optionally protected amino group, or bind together at the ends and form in association with the adjacent nitrogen atom an optionally substituted heterocyclic group. JP-09-59255A, (1993).

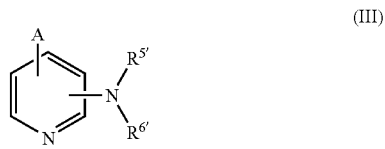

(III)

Wherein A is a group selected from those shown by the formulas:

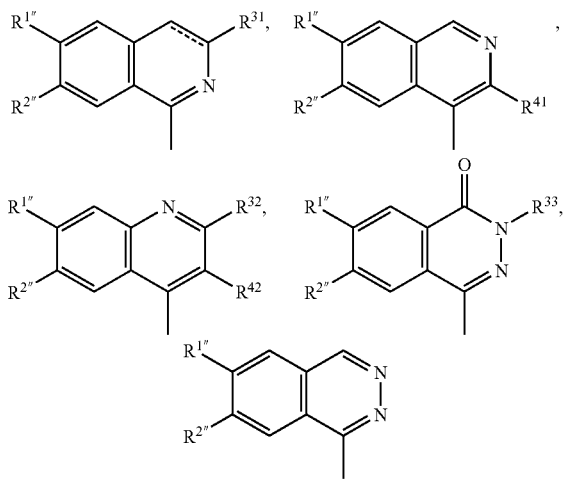

wherein $R^{1'''}$ and $R^{2'''}$ are the same or different and each a hydrogen atom or an optionally protected hydroxyl group; $R^{31}$ is an optionally protected hydroxymethyl group; $R^{32}$ is a hydrogen atom, a lower alkyl group or an optionally protected hydroxymethyl group; $R^{33}$ is an optionally substituted lower alkyl group; $R^{41}$ is an optionally protected hydroxymethyl group; $R^{42}$ is an optionally protected hydroxymethyl group; the dotted line represents the presence or absence of a double bond; and $R^{5'''}$ and $R^{6'''}$ are the same or different and each a hydrogen atom or an optionally protected amino group, or bind together at the ends and form in association with the adjacent nitrogen atom an optionally substituted heterocyclic group. JP-10-226685A (1998).

As a PDE4 inhibitor which is an active ingredient of the present composition for regenerative treatment of cartilage disease, among group (A), compounds having naphthalene or isoquinoline skeleton and pharmaceutically acceptable salts thereof are more preferred, and Compounds (1) and (2) and their pharmaceutically acceptable salts are still more preferred.

Since PDE4 inhibitors may cause vomiting or gastric acid secretion depending on dosage when acted systemically (Cellular Signaling, 9 (3-4), pp. 227-236 (1997)), the present composition for regenerative treatment of cartilage disease is preferably applied locally to a vicinity of affected region (especially, vicinity of articular cartilage), so that the drug concentration in the systemic blood does not increase but the one at the affected cartilage region is maintained. To establish this purpose, it is preferred to formulate the composition into a sustained release form which can advantageously reduce the frequency of administration and also decrease the burden of patients.

Examples of preferred embodiments of the present composition include depot preparations which gradually release a drug when administered locally (e.g., pellet preparation, gel preparation, matrix preparation, microsphere preparation, a sustained release preparation obtained by adding a drug into an aqueous solution of a biocompatible and biodegradable polymer, a preparation which is designed to be a liquid at the time of administration and to form a gel in a living body after administration, a preparation embedded in various bases which are reported to be generally used in the field of orthopedics, and the like.)

Examples of pellet preparations include a long-term sustained release preparation obtainable by compressing a drug and fine particles of lactic acid-glycolic acid copolymer of which terminal carboxyl group is esterified by an alcohol, and the like. (JP2001-187749A)

Examples of gel preparations include those obtained by dissolving into a phosphate buffer a drug and hyaluronic acid which is chemically bound to polyethylene glycol (Journal of Controlled Release, 59 (1999) pp. 77-86), and the like.

Examples of matrix preparations comprising a drug include those obtained by impregnating a drug into granular material of collagen or fibrous membrane preparation, or by adding a drug to a granular material of collagen or a reaction mixture for preparing a fibrous membrane preparation, and the like (JP10-182499A (1998), JP06-305983 (1994)).

Examples of a sustained release preparation obtained by adding a drug into an aqueous solution of a biocompatible and biodegradable polymer include those obtained by adding a drug into an aqueous sodium hyaluronate solution, and the like.

Examples of a preparation designed to be a liquid at the time of administration and to form a gel in a living body after administration include those wherein a drug and a lactic acid-glycolic acid copolymer are dissolved in N-methyl-2-pyrrolidone (Journal of Controlled Release, 33 (1995) pp. 237-243), or a preparation comprising a drug and a polymer that exists as an solution at low temperature but forms a gel at body temperature, such as a block co-polymer of lactic acid-glycolic acid copolymer and polyethylene glycol and the like (ibid., 27(1993), 139-147).

Examples of a preparation embedded in various bases which are reported to be generally used in the field of orthopaedics include those prepared by mixing a drug and a base (e.g., water-insoluble biocompatible and biodegradable polymer, polymethyl methacrylate, hydroxyapatite, tricalcium phosphate or the like). Biomaterials, vol. 21, pp. 2405-2412 (2000); and International Journal of Pharmaceutics, vol. 206, pp. 1-12 (2000).

Preparations for local administration that release an effective amount of PDE4 inhibitor gradually to a vicinity of cartilage region with a lesion(s) (especially, vicinity of articular cartilage) are preferred in the respect that the administration frequency during the term required for regenerative treatment of cartilage disease can be reduced.

Among depot preparations, in the case of microspheres feasible for local administration by injection, the particle size of such microspheres is preferably in the range suitable for passing a needle, more preferably 0.01-150 µm, particularly preferably 0.1-100 µm in the respect that the irritation at the affection site can be reduced.

Since the present composition for regenerative treatment of cartilage disease, which comprises a PDE4 inhibitor as an active ingredient, is administered locally to a vicinity of cartilage region with a lesion(s) (especially, vicinity of articular cartilage), it would be preferable to make the dosage small. Accordingly, the PDE4 inhibitor content in the composition such as microsphere preparation can be preferably 0.0001-80% by weight, more preferably 0.001-50% by weight, and further more preferably 0.01-50% by weight. The dose of a PDE4 inhibitor as an active ingredient may vary depending on the kind of PDE4 inhibitor to be used, the weight, age, conditions of the subject or a site to be applied and is generally determined by a physician; however, for local administration, the dose can usually be in the range of from 1 ng to 1 g per affected region.

The composition for regenerative treatment of cartilage disease of the present invention can be prepared in a conventional manner using a PDE4 inhibitor and a pharmaceutically acceptable excipient or a carrier therefor. Preferred composition can be prepared by combining a PDE4 inhibitor and a biocompatible and biodegradable polymer.

Among them, the water-insoluble biocompatible and biodegradable polymer is a water-insoluble biocompatible and biodegradable polymer that requires at least 1000 ml of water to dissolve 1 g of the polymer at 25° C., and specific example include hydroxy fatty acid polyesters and derivatives thereof (for example, poly lactic acid, poly glycolic acid, poly citric acid, poly, malic acid, poly-β-hydroxybutyric acid, ring-opening polymerized ε-caprolactones, lactic acid-glycolic acid copolymer, 2-hydroxybutyric acid-glycolic acid copolymer, block copolymer of poly lactic acid and polyethylene glycol, block copolymer of poly glycolic acid and polyethylene glycol, and block copolymer of lactic acid-glycolic acid copolymer and polyethylene glycol, etc.), polymers of alkyl α-cyanoacrylates (e.g., polybutyl-2-cyanoacrylate, etc.), polyalkylene oxalate (e.g., polytrimethylene oxalate, polytetramethylene oxalate, etc.), polyortho-esters, polycarbonates (e.g., polyethylene carbonate, polyethylenepropylene carbonate, etc.), polyortho-carbonates, polyamino acids (e.g., poly-γ-L-alanine, poly-γ-benzyl-L-glutamic acid, poly-γ-methyl-L-glutamic acid, etc.), hyaluronic acid esters. One or more of these polymers can be used. Other biocompatible and biodegradable Polymers include sodium hyaluronate, chondroitin sulfate, collagen, gelatin, fibrin, and the like.

Among the water insoluble biocompatible and biodegradable polymers above, hydroxy fatty acid polyesters are particularly preferred. Above all, those of which average molecular weight ranging in between 2000 and about 800000 are more preferred, those ranging in between 2000 and about 200000 are especially preferred and those ranging in between 5000 and 50000 are most preferred.

In addition, among the hydroxy fatty acid polyesters above, poly lactic acid, lactic acid-glycolic acid copolymer and 2-hydroxybutyric acid-glycolic acid copolymer are more preferred. The molar ratio of lactic acid and glycolic acid in a lactic acid-glycolic acid copolymer is preferably 90:10 to 30:70, more preferably 80:20 to 40:60, and the molar ratio of 2-hydroxybutyric acid and glycolic acid in a 2-hydroxybutyric acid-glycolic acid copolymer is preferably 90:10 to 30:70, more preferably 80:20 to 40:60.

When formulating a PDE4 inhibitor above into a depot preparation, it can be carried out appropriately depending on the intended embodiment, optionally after pulverizing a PDE4 inhibitor if necessary.

Pulverization of PDE4 inhibitor can be carried out using any one of conventional methods for producing fine particles including mechanical pulverization methods such as jet mill, hammer mill, convolution ball mill, jar ball mill, beads mill, shaker mill, rod mill and tube mill pulverizations, or so-called crystallization method wherein a drug is first dissolved in a solvent and then recrystallized by adjusting pH, changing temperature, or altering the constitution of solvent, and recovering the particles by centrifugation, filtration, or the like.

When preparing the above-mentioned various types of formulations of the present pharmaceutical composition, any appropriate process can be used depending on the selected PDE4 inhibitor.

For example, microsphere preparation can be prepared by the following methods. In case that a salt of a PDE4 inhibitor shows low incorporation rate into a microsphere, it may be converted into corresponding free form using an acid or a base prior to the preparation of microspheres.

(1) In-Water Drying Method

In this method, a drug is added to a solution of water-insoluble biocompatible and biodegradable polymer in a water-immiscible organic solvent of which boiling point is lower than water (water-insoluble polymer solution), and the resultant organic phase is dispersed into an aqueous phase to give an O/W emulsion, which is followed by removal of the organic solvent. This method can be conducted in a manner similar to those described in, for example, JP 56-19324B (1981), JP 63-91325A (1988), JP 08-151321A (1996), Kajeev Jain et al., "Controlled Drug Delivery by Biodegradable Poly (Ester) Devices: Different Preparative Approaches", Drug Development and Industrial Pharmacy, vol. 24(8), pp. 703-727, 1998, JP 60-100516A (1985), JP 62-201816A (1987), JP 09-221417A (1997) and JP 06-211648A (1994).

(2) Phase Separation Method

In this method, into a solution of water-insoluble biocompatible and biodegradable polymer in an organic solvent is dissolved or dispersed a drug, or is dispersed an aqueous solution of the drug. A hardening agent is then added gradually with stirring to obtain solid precipitations. This method can be conducted in a manner similar to those described in, for example, JP 60-67417A (1985), U.S. Pat. No. 5,503,851, U.S. Pat. No. 5,000,886, Eur. J. Pharm. Biopharm. vol. 42 (1), pp. 16-24 (1996) and the forecited Jain et al. (ibid.)

(3) Spray Drying Method

In this method, to a solution of water insoluble biocompatible and biodegradable polymer in an organic solvent is dissolved or dispersed a drug, or is dispersed an aqueous solution of the drug. The resultant solution or dispersion is then sprayed via a nozzle into a drying chamber of a spray drier to volatilize the organic solvent in the fine droplets in a very short time. This method can be conducted in a manner similar to those described in, for example, JP 01-155942A (1989), JP 05-194200A (1993), JP 05-70363A (1993), JP 08-151321A (1996), JP 09-221417A (1997), U.S. Pat. No. 5,922,253, "Spray Drying Handbook" (John Wiley & Sons, New York 1984), Partick B. Deasy, "Microcapsulation and Related Drug Processes" (Marcel Dekker, Inc., New York 1984) and the forecited Jain et al. (ibid), and the like.

(4) Solvent Diffusion Method

In this method, a solution of a drug and a water insoluble biocompatible and biodegradable polymer in a water miscible organic solvent is added to an aqueous solution of protective colloid, followed by emulsification with stirring to yield fine particles. This method can be conducted in a manner similar to those described in, for example, JP 05-58882A (1993), JP 09-110678A (1997) and International Journal of Pharmaceutics, vol. 187, pp. 143-152 (1999).

In the aforementioned "In-Water Drying Method", different preparation processes may be employed depending on the type of organic phase though they all can be conducted in a conventional manner. Examples of organic phase include the followings.

(a) An organic phase wherein a drug is directly dissolved or dispersed in a solution of a water-insoluble, biocompatible and biodegradable polymer. This, when dispersed in an aqueous phase, gives O/W emulsion (JP 56-19324B (1981), JP 63-91325A (1988), JP 06-32732A (1994), JP 08-151321A (1996), JP 06-32732A (1994), and the forecited Jain, etc.)

(b) An organic phase which is W/O emulsion wherein an aqueous solution of a drug is dispersed in a solution of a water-insoluble, biocompatible and biodegradable polymer. The W/O emulsion, when dispersed in an aqueous phase, gives (W/O)/W emulsion (JP 60-100516A (1985), JP 62-201816A (1987), JP 09-221417A (1997), and the forecited Jain, etc.)

(c) An organic phase which is O/O emulsion, which uses two or more water-insoluble, biocompatible and biodegradable polymers, wherein a drug is dissolved or dispersed in a polymer solution that is dispersed in the other(s). The O/O emulsion, when dispersed in an aqueous phase, gives (O/O)/W emulsion (JP 06-211648A (1994)).

By using any of the organic phases above, the emulsification can be achieved by a conventional method, for example, the intermittent shaking method, the method using a mixer such as a propeller shaker or a turbine shaker, the colloidal mill method, the homogenizer method and the ultrasonication method.

Examples of organic solvent usable in these methods include halogenated hydrocarbons (methylene chloride, chloroform, carbon tetrachloride, chloroethane, dichloroethane, trichloroethane, etc.), aliphatic esters (ethyl acetate, butyl acetate, etc.), aromatic hydrocarbons (benzene, etc.), aliphatic hydrocarbons (n-hexane, n-pentane, cyclohexane, etc.), ketones (methylethyl ketone, etc.), ethers (diethyl ether, diisopropyl ether, methyl isobutyl ether, etc.)

In preparation of emulsion above, an emulsifier may be added to an aqueous phase to stabilize emulsion, which emulsifier includes, for example, anionic surfactants (sodium oleate, sodium stearate, sodium lauryl sulfate, etc.), nonionic surfactants (polyoxyethylene sorbitan fatty acid ester [Tween80, Tween 60 (Nikko Chemicals, Co., Ltd.)], polyethylene castor oil derivatives [HCO-60, HCO-50 (Nikko Chemicals, Co., Ltd.)], polyvinylpyrrolidone, polyvinyl alcohol, carboxymethyl cellulose, methyl cellulose, lecithin, gelatin, etc.

Further, when one or more other ingredients are incorporated in addition to PDE4 inhibitor, the former can be preferably added to the organic phase at the time of preparation of O/W emulsion. To obtain a microsphere preparation with an elevated concentration of medicinal ingredient, it is necessary to prepare an organic phase containing an active ingredient at high concentration. For this purpose, an osmoregulatory agent may be included in an aqueous phase to prevent the outflow of an active ingredient into an aqueous phase (JP 2608245).

The O/W emulsion obtained in the above-mentioned manner is then subjected to in-water-drying to remove organic solvent present in emulsion to give microspheres.

Organic solvent can be removed from emulsion in a conventional manner such as heating, placing under reduced pressure, blowing air, or the like, and for example, a method where a solvent is distilled off in an open system (JP 56-19324B (1981), JP 63-91325A (1988), JP 08-151321A (1996), JP 06-211648A (1994)) or in a closed system (JP 09-221418A (1997)) can be employed. In addition, a method where a solvent is extracted and removed by means of a large quantity of outside water phase (JP-2582186) can also be used.

Further, the following methods can be appropriately used depending on the PDE4 inhibitor.

A method wherein a solution containing a drug, a biodegradable polymer and a water-miscible good solvent (Solvent A: acetone, tetrahydrofuran, etc.) for the said polymer is first added to a homogeneous mixed solution comprising a poor solvent (Solvent B: water, ethanol, etc.) for the said polymer, which is miscible with solvent A, and a poor solvent (Solvent C: glycerin, etc.) for the said polymer, which is immiscible with solvent A. The mixture, upon emulsification, gives emulsion wherein the polymer solution constitutes the dispersed-phase and the homogeneous mixed solution constitutes the continuous-phase. The solvent A is then removed from the dispersed phase (WO/01/80835).

A method for preparing microspheres from emulsion by in-water-drying method, in which emulsion an organic phase containing an organic solvent with a boiling point lower than water (methylene chloride, ethyl acetate, etc.) and a water insoluble polymer is emulsified in an aqueous phase, comprising (1) employing a device equipped with a gas separation membrane (permeable evaporation membrane, porous membrane, etc.), (2) providing emulsion to be subjected to the in-water-drying to one side of the gas separating membrane, and (3) distilling off the organic solvent in emulsion to the other side of the gas separating membrane (WO/01/83594).

Furthermore, the organic solvent remaining in microspheres can be removed by heating microspheres in an aqueous phase at temperature higher than the boiling point of the organic solvent (JP 2000-239152A) or heating the microspheres to dry after coating With an additive of high melting point (JP 09-221417A (1997)).

The resultant microspheres are recovered by centrifugation, filtration or sieving, washed to remove substances attached on the surface such as additives in the water-phase, and subjected to lyophilization optionally after combining with an aggregation inhibitor to prevent the agglomeration of microspheres, for example, sugar, sugar alcohol or, inorganic salt, preferably lactose, mannitol or sorbitol. It is preferred to use a sieve to obtain microspheres of an intended particle size, and it is more preferred to use a sieve allowing particles of, for example, 150 µm or below to pass so as to improve the syringeability when the microsphere preparation is used as injectable solution.

For preparing microspheres by "Phase Separation Method", amphiphilic solvents such as acetone, acetonitrile, tetrahydrofuran and dioxane in addition to the organic solvents used in the "In-water Drying Method" above can be used. A PDE4 inhibitor and optionally one or more additional ingredients, or a solution thereof, are dissolved or dispersed in an organic solution of water insoluble polymer in any one of these organic solvents to form an organic phase. The organic phase is added gradually to a solvent (disperse medium) immiscible with the organic solvent above, for example, silicon oil, liquid paraffin, sesame oil, soybean oil, corn oil, cotton seed oil, coconuts-oil, linseed oil, with stirring to form O/O emulsion. If desired, a surfactant may be added to the disperse medium. The water insoluble polymer can be solidified by cooling the emulsion or evaporating the solvent in the organic phase by heating. Alternatively, a hardening agent such as hexane, cyclohexane, methyl ethyl ketone, octamethyl-cyclotetrasiloxane or the like can be added gently to emulsion with stirring, or vice versa, to separate out the water insoluble polymer from emulsion thereby forming microspheres.

The resultant microspheres are recovered by centrifugation, filtration or sieving, washed with hexane or purified water to remove solvents, additives, etc. attached on its surface, and optionally subjected to air-drying, vacuum-drying, or lyophilization. Alternatively, it can be lyophilized after adding an aggregation inhibitor in a manner similar to that used in the above-mentioned in-water-drying method.

Examples of internal organic phase in the phase separation method include the following embodiments.
(a) An organic phase wherein a drug is directly dissolved or dispersed in a solution of a water-insoluble, biocompatible and biodegradable polymer.
(b) An organic phase which is W/O emulsion wherein an aqueous solution of a drug is dispersed in a solution of a water-insoluble, biocompatible and biodegradable polymer.
(c) An organic phase which is O/O emulsion, which uses two or more water-insoluble, biocompatible and biodegradable polymers, wherein a drug or a solution thereof is dissolved or dispersed in a polymer solution that is dispersed in the other(s).

Further, the preparation of microspheres by "Spray Drying Method" is conducted using the same organic solvent as the above-mentioned phase separation method. To an organic solvent is dissolved a water insoluble biocompatible and biodegradable polymer, and a PDE4 inhibitor and optionally one or more additional ingredients, or a solution thereof, are dissolved or dispersed in the solution, and sprayed via a nozzle into a drying chamber of a spray drier to volatilize the organic solvent to form microspheres.

For the present invention, any commercially available spray dryers, for example, such as Pulvis Mini Spray GS31 (YAMATO Scientific Co., Ltd.), Mini Spray Dryer (Shibata Scientific Technology Ltd.), can be used.

The resultant microspheres are then worked-up in a manner similar to that used in the in-water drying method to yield the desired microsphere preparation.

Examples of water-miscible organic solvents usable in the "Solvent Diffusion Method", include acetone, methanol, ethanol or a mixture thereof, which may further contain a volatile solvent (methylene chloride, chloroform) in which a drug can dissolve, if necessary. Examples of colloid protective agent include polyvinyl alcohol.

When the microsphere preparation of the present composition for regenerative treatment of cartilage disease, which comprises a PDE4 inhibitor as an active ingredient, is administered to a vicinity of affected region (especially, in the articular cartilage), it can be preferably applied locally, more preferably, into articular cartilage as injection or implant.

An injectable preparation of microspheres can be prepared by dispersing/suspending microspheres obtained by the present invention at a concentration of 0.0001-1000 mg/ma, preferably 0.0005-800 mg/ml, more preferably 0.001-500 mg/ml into an aqueous solution containing a dispersant.

Examples of dispersant include nonionic surfactants such as polyoxyethylene sorbitan fatty acid ester (Tween80, Tween60, Nikko Chemicals Co, Ltd.), polyethylene castor oil (HCO-60, HCO-50, Nikko Chemicals Co., Ltd.), cellulose-derived dispersants such as carboxymethyl cellulose sodium, sodium alginate, dextran, sodium hyaluronate, and the like. These dispersants can serve to improve the dispersibility of microspheres and stabilize the elution of an active ingredient. A dispersant can generally be added to a composition at a concentration of 0.01-2% by weight preferably 0.05-1% by weight.

The injectable preparation above may optionally contain a preservative (methylparaben, propylparaben, benzyl alcohol, chlorobutanol, sorbic acid, boric acid, amino acid, polyethylene glycol, etc.), an isotonizing agent (sodium chloride, glycerin, sorbitol, glucose, mannitol, etc.), a pH modifier (sodium hydroxide, potassium hydroxide, hydrochloric acid, phosphoric acid, citric acid, oxalic acid, carbonic acid, acetic acid, arginine, lysine, etc.), a buffer (sodium hydrogen phosphate, potassium hydrogen phosphate, etc.) or the like.

If necessary, a steroid antiinflammatory analgesic or non-steroidal antiinflammatory analgesic may be dissolved or dispersed in the injectable preparation. Examples of steroidal antiinflammatory analgesic include dexamethasone, triamcinolone, triamcinolone acetonide, halopredone, paramethasone, hydrocortisone, prednisolone, methylprednisolone, betamethasone, and the like. Examples of non-steroidal antiinflammatory analgesic include ibuprofen, ketoprofen, indomethacin, naproxen, piroxicam, and the like.

In addition to the above-mentioned suspension, the microsphere injection containing PDE4 inhibitor can be in the form of a kit for preparing an injectable preparation at the time of use, which kit comprises a solid preparation of an aggregation inhibitor and microspheres, a dispersant and injectable distilled water.

The solid preparation used in a kit can be prepared by suspending microspheres in an aqueous solution containing an aggregation inhibitor, and subjecting the suspension to lyophilization, vacuum drying, spray drying, and/or the like. The lyophilization is especially preferred.

When preparing a solid preparation, a dispersant can be added to an aqueous solution containing aggregation inhibitor (mannitol, sorbitol, lactose, glucose, xylitol, maltose, galactose, sucrose, etc.) in order to improve the re-dispersibility into injectable distilled water, thereby yielding a solid preparation of good dispersibility. If necessary, it can be formulated into a kit for preparing an injectable preparation, in which a steroidal antiinflammatory analgesic and/or a non-steroidal antiinflammatory analgesic as well as a dispersant are combined.

The present composition for regenerative treatment of cartilage disease, which comprises a PDE4 inhibitor as an active ingredient, can be used in treatment of various warm blood mammals such as human, a domestic animal (a horse, a bull, a sheep, a pig), a pet (a dog, a cat), and the like. The composition for regenerative treatment of cartilage disease can be used in regenerative treatment of various cartilage diseases such as osteoarthrosis, chondrodystrophy, degenerative discopathy, meniscus injury or the like, and be preferably used in regenerative treatment of osteoarthrosis.

EXAMPLES

The following Experimental Examples, Examples and Test Examples are provided to further illustrate the present invention. Throughout the following examples, a compound with a given number is the same compound indicated by the same number in the list above which shows specific examples of preferred compounds with chemical structure.

Experimental Example 1

Increase of Matrix Production of Articular Chondrocytes

| Test Compounds | |
|---|---|
| Compound (1) | ($10^{-5}$ M or $10^{-4}$ M); |
| Compound (2) | ($10^{-6}$ M or $10^{-5}$ M); |
| Compound (9) | ($10^{-6}$ M or $10^{-5}$ M); |
| Compound (11) | ($10^{-6}$ M); |
| Compound (21) | ($10^{-6}$ M or $10^{-5}$ M); |
| Compound (27) | ($10^{-6}$ M or $10^{-5}$ M); |
| Compound (44) | ($10^{-5}$ M or $10^{-4}$ M); |

(Isolation and Maintenance of Articular Chondrocytes)

Four NZW line rabbits (Kitayama Labes., Co Ltd.; male; 4-week-old) were sacrificed with bleeding under ether anesthesia and femur knee joints were collected aseptically. The collected knee joints were stored in phosphate buffer (pH 7.2) containing 0.2% glucose and only the cortical layer of knee joint was scrapped with a surgical knife into a 50 ml tube containing phosphate buffer (pH 7.2) containing 0.2% glucose. The collected knee joint cortical layer was cut into as small sections as possible on a dish with a razor and shaken at 37° C. for 15 minutes in phosphate buffer containing 0.2% glucose, supplied with 10× trypsin-ethylenediamine tetraacetic acid (EDTA)·4 Na salt (GIBCO; Cat. No. 15400-054) (50 ml, with 100 mg of trypsin and 40 mg of EDTA·4Na; pH 7.2). After shaking, the sample was centrifuged (1,400 rpm) to collect precipitates, and the precipitates were washed twice with 40 ml of phosphate buffer containing 0.2% glucose. The washed precipitates were combined with 40 ml of serum-free α-minimum essential medium (MEM: GIBCO; Cat: No. 12571-063) containing 60 mg of collagenase for cell diffusion (Wako Pure Chemical Industries, Ltd., 034-10533) and transferred to a 100 ml beaker containing a sterilized stirrer bar. Under stirring with the stirrer bar, the collagenase digestion was carried on for about 1 hour in a $CO_2$ incubator at 37° C. Cartilage fragments were removed from the collagenase-treated cells using a 40 μM Cell Strainer ([FALCON; Cat. No. 2340]). To the residual treated cells was added 10 ml of α-MEM medium containing 10% fetal calf serum (FCS), and centrifuged (1,400 rpm). The precipitates were washed with 10% FCS-αMEM medium twice, suspended in appropriate volume of the same medium and the resultant suspension was seeded into collagen type II (Wako Pure Chemical Industries, Ltd., 033-13901)-coated plates (48 well) at 20,000 cells/well. On the next day, the medium was replaced with 10% FCS-αMEM medium.

(Increase of Matrix Production)

When cells reached to confluent after the medium exchange procedure above, the medium for test group was replaced with test compound-containing medium (including 0.1% dimethylsulfoxide as a vehicle). As a medium to which a test compound is added, 10% FCS-αMEM medium containing 0.2 mM ascorbic acid was used. The day on which test compound-containing medium was added for the first time was defined as "day 1". The medium exchange with the same medium was again conducted at day 3 and the cultivation continued until day 5. As to the control group, the medium was exchanged at the same time using the same medium as the test group except that it is free of test compound (containing vehicle only), and the cultivation was carried out in the same manner. After completion of cultivation, the supernatant was removed from the culture medium. Cells were fixed by addition of 0.25 ml of neutral buffer containing 4% paraformaldehyde and incubation for 2 hours. Cells were washed three times with 1 ml of phosphate buffer (pH 7.2) and then stained for 4 hours with 0.1% Alcian blue 8GX (Sigma; A3157) dissolved in 0.1 M hydrochloric acid, which Alcian blue selectively stains cartilage matrix proteoglycan. After staining, the cells were washed 3 times with 1 ml of phosphate buffer (pH 7.2). Alcian blue which had stained cartilage matrix was dissolved with 0.25 ml of aqueous 6 M guanidine hydrochloride solution and a portion of the solution was used to determine the absorbance at 620 nm. The amounts of Alcian blue used for staining was calculated from the absorbance, which in turn was used for the estimation of the amount of matrix (proteoglycan). The results are shown in Table 1.

TABLE 1

| Test Compound | Concentration (M) | Proteoglycan Production (%) |
|---|---|---|
| Vehicle | — | 100 |
| Compound(1) | $1 \times 10^{-5}$ | 133 |
| | $1 \times 10^{-4}$ | 144 |
| Compound(2) | $1 \times 10^{-6}$ | 125 |
| | $1 \times 10^{-5}$ | 128 |
| Compound(9) | $1 \times 10^{-6}$ | 128 |
| | $1 \times 10^{-5}$ | 138 |
| Compound(11) | $1 \times 10^{-6}$ | 112 |
| Compound(21) | $1 \times 10^{-6}$ | 115 |
| | $1 \times 10^{-5}$ | 120 |
| Compound(27) | $1 \times 10^{-6}$ | 129 |
| | $1 \times 10^{-5}$ | 131 |
| Compound(44) | $1 \times 10^{-5}$ | 125 |
| | $1 \times 10^{-4}$ | 116 |

As shown in Table 1 above, it was demonstrated that all the test compounds (Compounds (1), (2), (9), (11), (21), (27) and (44)) having PDE4 inhibitory activity exert matrix production promoting activity.

Experimental Example 2

Fractionation of cAMP-Hydrolyzing PDE Expressed in Articular Cartilage

Four NZW line rabbits (Kitayama Labes., Co Ltd.; male; 4-week-old) were sacrificed with bleeding under ether anesthesia and femur knee joints were collected aseptically. The collected knee joints were stored in phosphate buffer (pH 7.2) containing 0.2% glucose and only the cortical layer of knee joint portion was scrapped with a knife into a 50 ml tube containing phosphate buffer (pH 7.2) containing 0.2% glucose. The collected knee joint cortical layer was cut into as small sections as possible on a dish with a razor, washed with ice-cold phosphate buffer and homogenized with a homogenizer (Polytron: Kinematica A.G.) in homogenization buffer (20 mM Tris-HCl, pH 7.4, 2 mM magnesium acetate, 0.3 mM calcium chloride, 1 mM dithiothreitol, 40 μM leupeptin, 1.3 mM benzamidine, 0.2 mM phenylmethylsulfonyl fluoride and 1 mM sodium azide). The resultant homogenate was centrifuged (100,000×g, 60 minutes) to separate supernatant.

The supernatant was subjected to Mono Q Sepharose High Performance column (Amersham Pharmacia Biotech) previously equilibrated with an elution buffer (20 mM Tris-HCl, pH 7.4, 1 mM calcium chloride, 1 mM dithiothreitol, 2 μM leupeptin, 5 mM benzamidine). After washing the column with 20 ml of elution buffer, proteins were eluted into 1 ml fractions by sodium chloride gradient under ice-cooling. Each fraction was subjected to the determination of cAMP hydrolyzing activity (PDE activity) on as a substrate.

The determination of PDE activity was performed by a radio-labeled nucleic acid assay. That is, the reaction was initiated by adding from 10 to 30 μl of elution fraction to 500 μl of assay buffer [50 mM Tris-HCl, pH 8.0, 5 mM magnesium chloride, 4 mM 2-mercaptoethanol, 0.33 mg/ml fetal bovine albumin (fatty acid-free, Sigma), 1 mM ethyleneglycol bis(β-aminoethylether)-N,N,N',N'-tetraacetic acid] containing 1 μM of unlabeled cAMP and 22 μM of [$^3$H]-cAMP (Amersham Pharmacia Biotech). For the control group, no drug was added while for the test group, Compound (44) was added at a final concentration of $1 \times 10^{-5}$ M. After incubation at 37° C. for 30 minutes, the reaction was quenched by boiling for 1.5 minutes. Then, 100 μl of 1 mg/ml Crtalus atrox snake venom was added and incubated at 37° C. for 30 minutes. After addition of 500 μl of methanol, the reaction mixture was subjected to Dowex column (1×8-400). To each eluate was added a liquid scintillation cocktail and the radio activity was measured. The results are shown in FIG. 1.

FIG. 1 shows that there are four peaks showing strong cAMP hydrolyzing activity. These four peaks fulfill the features of: (1) having hydrolytic activity selective to cAMP; (2) said cAMP hydrolyzing activity being free from the influence of cGMP; and (3) said activity being strongly inhibited by Compound (44) that is a selective PDE4 inhibitor, and hence were considered to be PDE4-related peaks. It was reported that PDE4 includes four subtypes, that is, PDE4A, PDE4B, PDE4C and PDE4D (Saldou et. al., Cellular Signaling, Vol. 10, 427-440, 1998), and these four peaks were assumed to be such subtypes or splicing variants originated therefrom.

Experimental Example 3

Expression of a Gene Encoding Cartilage Matrix Protein

Total RNA was extracted with ISOGEN (Nippon Gene Co., Ltd.) from rabbit knee articular chondrocytes cultured for 4 days according to the same manner as Experimental Example 1 in the presence of Compound (1) at a final concentration of $1 \times 10^{-4}$ M or $1 \times 10^{-5}$ M, and 15 μg of the total RNA was dissolved in 4.5 μl of a sterilized water. This solution was combined with 2 μl of 5×MOPS buffer, 3.5 μl of formaldehyde and 10 μl of formamide, and denatured at 90° C. for 15 minutes. The mixture was then electrophoresed on 1% agarose gel in the presence of formaldehyde. After completion of electrophoresis, RNA was transferred to a nylon membrane (Amersham Pharmacia Biotech) overnight by capillary method. The RNA was fixed to the nylon membrane by UV crosslinking and subjected to prehybridization at 60° C. for 2 hours in 50 ml of hybridization solution (6×SSC, 5×Denhart's solution, 0.5% SDS, 100 μg/ml heat-denatured salmon sperm DNA, free of 50% formamide).

Then, DNA probes of mouse type II collagen gene and human aggrecan. (typical protein consisting proteoglycan) gene were respectively radio-labeled with α[$^{32}$P]dCTP using Random-Prime Labeling Kit Ver. 2 (Amersham Pharmacia Biotech). Each probe ($1 \times 10^8$ dpm) and 5 ml of hybridization solution were added to a prehybridized nylon membrane and sealed, and allowed to hybridize at 60° C. overnight. The nylon membrane was washed with a solution containing 0.2× SSC and 0.2% sodium dodecyl sulfate at 60° C. for 40 minutes three times. The nylon membrane was subjected to an autoradiography and exposed to X-ray film using LAS-1000 (Fuji Photo Film Co., Ltd.) A relative amount of each RNA was measured using Image Gause (Fuji Photo Film Co., Ltd.) and corrected with 283 RNA (internal RNA: internal control). The gene expression rate in test group was calculated by assuming that in control group as 100%. The results are shown in Table 2.

TABLE 2

|  | Expression of Type II collagen gene (%) | Expression of aggrecan gene (%) |
| --- | --- | --- |
| Control | 100 | 100 |
| Compound(1) $10^{-5}$ M | 278 | 2693 |
| Compound(1) $10^{-4}$ M | 406 | 4262 |

As shown in Table 2 above, in the test group wherein a PDE4 inhibitor (Compound (1)) was added, the expression of type II collagen and aggrecan genes increased in a dose-dependent manner, which indicated that a PDE4 inhibitor affects articular chondrocytes so as to increase gene expression of type II collagen and aggrecan, which are major components of articular cartilage matrix, and thereby promoting the cartilage matrix production.

Experimental Example 4

Increase of Knee Articular Cartilage Matrix in Old Rabbit (Acclimation)

Old JW line rabbits (Kitayama Labes., Co Ltd.; male; 37-week-old) were housed at room temperature (23±2° C.) and 50±20% humidity. During the housing period, the rabbits were free to access commercially available food (Oriental Bio; CE-2).

(Increase of Articular Cartilage Matrix Production)

The rabbits were anesthetized by an intravenous injection of Nembutal (Dainabot Co., Ltd.; 50 mg/kg/ml) into an ear vein. The left knee articular cartilage portion was shaved and sterilized with 70% aqueous ethanol. For the test groups, 250 μl of the test compound-containing microsphere dispersion (drug content: 2.5 mg) prepared in Example 2-(3) was injected intra-articularly with a 18 gage needle (Terumo Corporation). For the control group, 250 μl of test compound-free microsphere dispersion prepared in Control Example 1-(2) was injected intra-articularly. At 14 days after administration, rabbits were sacrificed with bleeding under Nembutal anesthesia. The knee joints were isolated, fixed in neutral buffer containing 10% formaldehyde and decalcified with aqueous 0.5 M EDTA-4Na solution to obtain sections. The sections were stained with 0.1 M hydrochloric acid containing 0.10% Alcian blue 8GX (Sigma; A3157) which selectively stains cartilage matrix (proteoglycan) and the stainability between the test and control groups was compared microscopically. As a result, the thickness of the matrix layer (proteoglycan), which was stained with Alcian blue, was more than three times in test groups compared with the control groups.

Experimental Example 5

Regeneration of Knee Articular Cartilage Matrix in Old Rabbit (Acclimation)

Old JW line rabbits (Kitayama Labes., Co Ltd.; male; 37-week-old) were housed at room temperature (23±2° C.)

and 50±20% humidity in a rabbit cage (C type: W370×D520× H330). During the housing period, the rabbits were free to access commercially available food (Oriental Bio; CE-2).
(Regeneration of Articular Cartilage)

The rabbits were anesthetized by an intravenous injection of Nembutal (Abbott Laboratories; 50 mg/kg/ml) into an ear vein. The left knee articular cartilage portion was shaved and sterilized with 70% aqueous ethanol. The median ligament of left knee was incised to expose the femur head and meniscus, and the bleeding from neighbor tissue was stopped with sterilized cotton. A hole (2 mm diameter and 3 mm depth) was bored in the hollow at the middle of femoral head (un-loaded portion) with a drill (TOYO Associates LTD.: Mr. Meister). The hole was washed with sterilized saline to remove bone scraps etc. generated during boring. The articular capsule and median ligament were sutured with silk thread and hemostasis and disinfection were conducted with sterilized cotton. Nine days later, for the test groups, 250 µl of the test compound-containing microsphere dispersion (drug content: 2.5 mg) prepared in Example 2-(3) was injected intra-articularly with a 18 gage needle (Terumo Corporation). For the control group, 250 µl of test compound-free microsphere dispersion prepared in Control Example 1-(2) was injected intra-articularly. Rabbits were sacrificed 14 days after administration with bleeding under Nembutal anesthesia. The knee joints were isolated, fixed in neutral buffer containing 10% formaldehyde and decalcified with aqueous 0.5 M EDTA-4Na solution to obtain sections. The degree of regeneration at the hole was observed microscopically. The results are shown in FIG. 2. As shown in FIG. 2, an advanced regeneration of hole was confirmed clearly in the test groups compared with the control group.

Experimental Example 6

Regenerative Healing Effects on Papain-Induced Gonarthrosis (Acclimation)

Japanese White rabbits (Kitayama Labes., Co Ltd.; male; 13-week-old) were housed for 8 days at room temperature (23±2° C.) and 50±20% humidity. During the housing period, the rabbits were fed with commercially available food (RC4, Oriental Yeast, Co., Ltd.) at the rate of about 140 g/day.
(Regenerative Healing Effect)

The rabbits were anesthetized by an intravenous injection of Nembutal (Abbott Laboratories Lot. 791102) into an ear vein. The both knee portions were shaved and sterilized with 70% aqueous ethanol. The rabbits received injections of 0.5 ml of aqueous saline solution containing 0.8% papain (Merck EC 3.4.22.2 lot 587644 019) twice into both knee joints at an interval of five days. One week after the second injection, for the test group, the microsphere dispersion prepared in Example 2-(3) (containing 0.2 or 2 mg of Compound (1)) was injected intra-articularly (left knee; 4-6 rabbits/group). For the control group, compound-free microsphere dispersion prepared in Control Example 1-(2) was injected intra-articularly (right knee; 4-6 rabbits/group) in the same amount as the dispersion used in test group. Furthermore, for the Artz-treated group, 0.3 ml of 1% aqueous hyaluronic acid sodium salt solution (Artz, Kaken Pharmaceutical Co., Ltd.) was injected intra-articularly (left knee; 2 rabbits per group). For the non-Artz treated group, 0.3 ml of saline was injected intra-articularly (right knee; 2 rabbits per group). To both of the Artz-treated and non-Artz-treated group, the same intra-articular injection as the above was conducted weekly four times in total. Four weeks after the last injection, rabbits were sacrificed with bleeding under ether anesthesia, knee joints were isolated and fixed in neutral buffer containing 10% formaldehyde. As a result, it was observed that the papain treatment caused an articular cartilage degeneration characterized by the irregularity of articular cartilage surface, decreased hematoxylin and eosin stainability, cartilage matrix fibrosis and disappearance of articular chondrocytes. Although a slight inhibition in the decrease of hematoxylin and eosin stainability was observed in the Artz-treated group, remarkable regenerating effects could not be confirmed. On the other hand, in the test group, wherein Compound (1)-containing microsphere was administered, showed great improvement of the above-mentioned pathological symptoms. In the control group or non-Artz treated group, recovering effects were not observed at all.

Experimental Example 7

Fractionation of cAMP Hydrolytic PDE Expressed in Human Articular Cartilage

From the human knee articular cartilage was isolated on surgery of osteoarthrosis patients. Cartilage portion was scrapped with a surgery knife, washed with ice-cold phosphate buffer and stored at −80° C. The cartilage tissues were milled at −80° C. and then, scattered into pieces with homogenizer (Kinematica A.G., Polytron) in ice-cold homogenization buffer (20 mM Tris-HCl, pH 8.0, 1 mM ethylene glycol bis(β-aminoethylether)-N,N,N',N'-tetraacetic acid, 1 mM dithiothreitol, 10 µg/ml leupeptin, 5 mM benzamidine, 0.2 mM phenylmethylsulfonyl fluoride, 1 mM sodium azide and 5 mM mercaptoethanol). The resultant homogenate was centrifuged (100,000×g; 30 minutes) to separate supernatant.

The above supernatant was loaded on a Mono Q Sepharose High Performance column (Amersham Pharmacia Biotech) equilibrated with elution buffer (20 mM Tris-HCl, pH 8.0, 1 mM ethylene glycol bis(β-aminoethylether)-N,N,N',N'-tetraacetic acid, 1 mM dithiothreitol, 2 µg/ml leupeptin, 5 mM benzamidine). After washing the column with 20 ml of elution buffer, proteins were eluted into 1 ml fractions by aqueous sodium chloride solution (concentration gradient: 0 to 1000 mM, 70 ml) under ice-cooling. Each fraction was subjected to the determination of hydrolytic activity (PDE activity) toward cAMP and cGMP as a substrate.

The determination of PDE activity was performed by a radio-labeled nucleic acid assay. That is, the reaction was initiated by adding from 10 to 50 µl of elution fraction to 500 µl of assay buffer (50 mM Tris-HCl, pH 8.0, 5 mM magnesium chloride, 4 mM 2-mercaptoethanol) containing 1 µM of unlabeled cAMP and 22 nM of [$^3$H]-cAMP (Amersham Pharmacia Biotech).

After incubation at 37° C. for 30 minutes, the reaction was quenched by boiling for 1.5 minutes. Then, 100 µl of 1 mg/ml Crtalus atrox snake venom was added and incubated at 37° C. for 30 minutes. After addition of 500 µl of methanol, the reaction solution was subjected to Dowex column (1×8-400). To each eluate was added a liquid scintillation cocktail and the radio activity was measured. The results are shown in FIG. 3.

Figure 3:
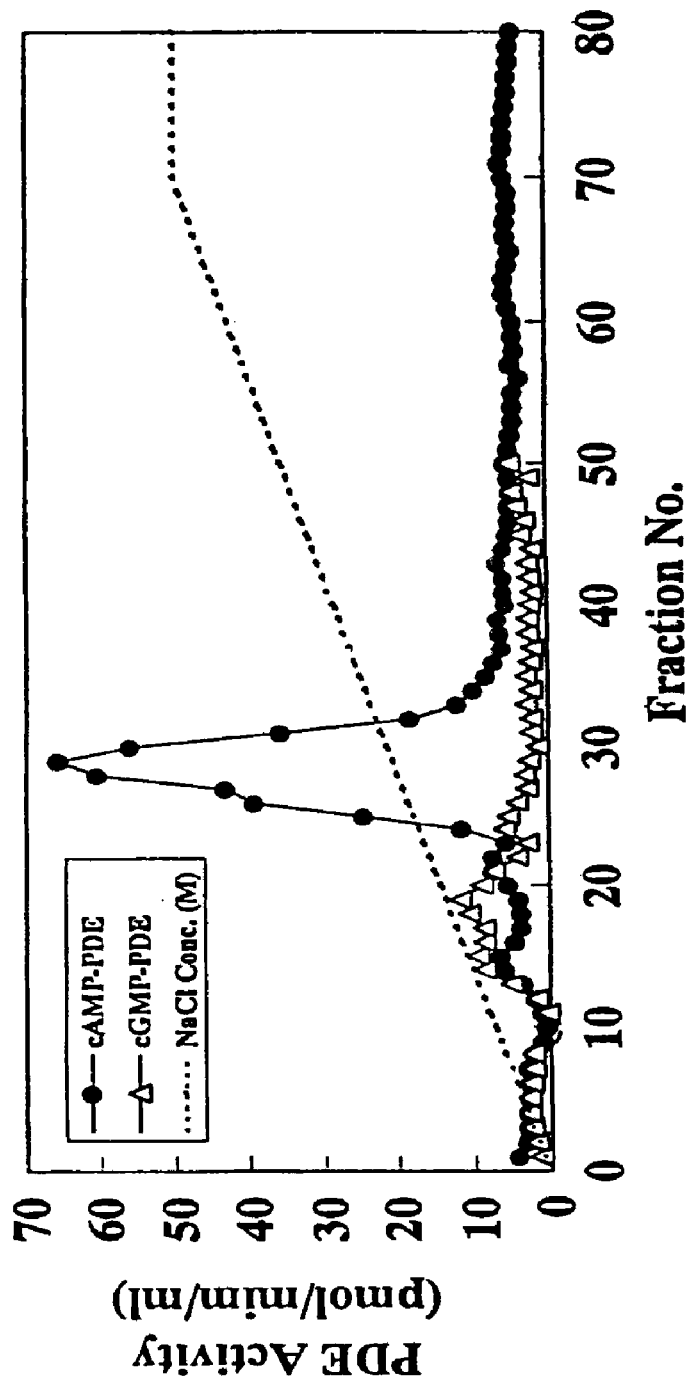
FIG. 3 is a graph showing the cAMP or cGMP hydrolyzing activity in each fraction obtained by fractionating human articular chondrocyte extract by Mono Q Sepharose column chromatography.

As shown in FIG. 3, it was revealed that, in a sample solution prepared by treating human cartilage derived from osteoarthrosis patient, no fractions having cGMP hydrolyzing activity exist, while fractions with potent cAMP hydrolyzing activity do.

The inhibitory activity of PDE4 inhibitor on fraction Nos. 28-30 containing potent cAMP hydrolyzing activity was measured according to the above-mentioned radio-labeled nucleic acid assay. The test compounds are Compound (1), Compound (2), Compound (11), Compound (44) and Compound (27).

Figure 4:
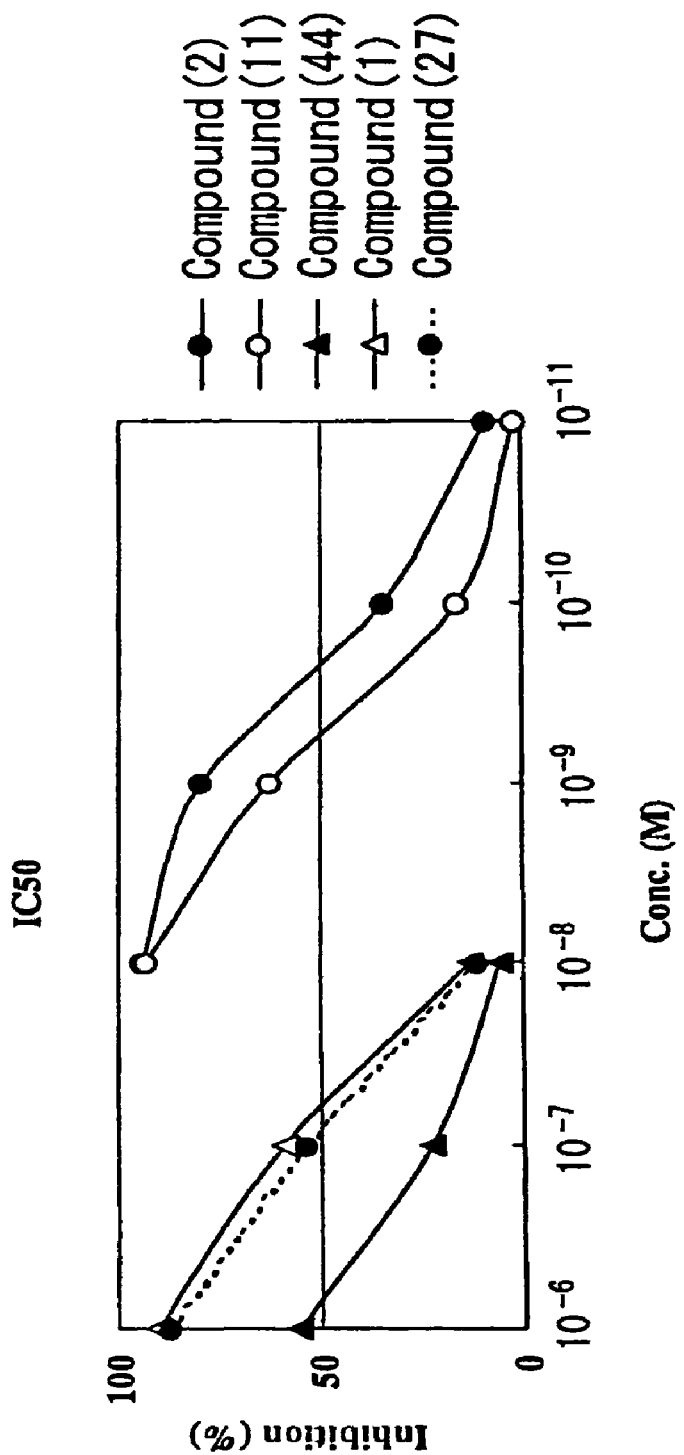
FIG. 4 is a graph showing the inhibitory activity ($IC_{50}$) of PDE4 inhibitor toward fractions 28-30 that showed potent cAMP hydrolyzing activity as demonstrated in FIG. 3.

As a result of experiments, it was confirmed that Compound (1) and Compound (2), in particular Compound (2) inhibits the hydrolytic activity of the fraction strongly. Further, the $IC_{50}$ of Compound (1) and Compound (2) for fraction(s), which was measured according to a method described in Journal of Medicinal Chemistry, vol. 42, 1088-1099 (1999), was consistent with the $IC_{50}$ of PDE4 inhibition activity described in the same literature. The results are shown in FIG. 4.

Experimental Example 8

Increase of Intracellular cAMP in Human Articular Chondrocytes (Isolation of Articular Chondrocytes)

Human articular cartilage (articular cartilage of degenerative malum coxae patient) was soaked in phosphate buffer (pH 7.2) and only the cortical layer of the joint portion was scrapped with, a knife into a 50 ml tube containing same buffer. The collected knee joint cortical layer was cut into as small sections as possible on a dish with a razor and transferred to a centrifuge tube.

To the centrifuge tube, phosphate buffer (pH 7.2) containing 1 mg/ml of hyaluronidase (SIGMA: Cat. No. H-3506) was added and shaken at 37° C. for 15 minutes. The precipitates were separated by centrifugation (2,000 rpm, 5 minutes) and added to Hank's balanced salt solution (GIBCO; Cat. No. 15050-065) containing 0.25% trypsin and shaken at 37° C. for 30 minutes.

After separation of precipitates by centrifugation (2,000 rpm, 5 minutes), α-minimum essential medium (GIBCO; Cat. No. 12571-063) containing 0.25% collagenase for cell diffusion (Wako Pure Chemical Industries, Ltd., 034-10533) and 10% fetal calf serum (GIBCO; Cat. No. 10099-141) were added to the precipitates and shaken at 37° C. overnight.

Cartilage fragments were removed using a 40 μm Cell Strainer (FALCON; Cat. No. 2340), and α-minimum essential medium containing 10% fetal calf serum was added to the collagenase-treated cells and centrifuged (1,400 rpm, 10 minutes).

The precipitates were washed three times with α-minimum essential medium containing 10% fetal calf serum and suspended in the same medium to an appropriate volume and seeded into 48-well plates (50,000 cells/well). On the next day, the medium was replaced with α-minimum essential medium containing 10% fetal calf serum. The α-minimum essential medium used contained antibiotics (100 U/ml penicillin G and 100 μg/ml streptomycin sulfate) and an antifungal (0.25 μg/ml amphotericin B) (GIBCO; Cat. No. 15240-062).

(Increase of Intracellular cAMP Concentration)

When cells reached to confluent after the medium exchange procedure above, the medium for test group was replaced with α-minimum essential medium containing 10% fetal calf serum (including 0.1% dimethylsulfoxide) supplied with 1 μM $PGE_2$ (SIGMA, Cat. No. P-0409) and $10^{-6}$ M or $10^{-5}$ M test compound. As to the control group, the medium was replaced with α-minimum essential medium (including 0.1% dimethylsulfoxide) containing 10% fetal calf serum supplied with 1 μM $PGE_2$ (SIGMA, Cat. No. P-0409).

After 30 minutes cultivation, medium was discarded. The resulting culture was washed with phosphate buffer (pH 7.2) and treated with 50% ethanol for 30 minutes. Ethanol was collected and the ethanol extract was evaporated to dryness. The residue was dissolved in an assay buffer attached with cAMP EIA system (Amersham Pharmacia Biotech; Cat. No. RPN225) and cAMP concentration was measured with said system. The results are shown in Table 3.

TABLE 3

| Test Compound | Concentration | $PGE_2$ (1 μM) | cAMP Production (picomol/well) |
|---|---|---|---|
| Vehicle | 0 | + | 0.4 |
| Compound(2) | $1 \times 10^{-6}$ | + | 13.8 |
| | $1 \times 10^{-5}$ | + | 23.2 |
| Compound(11) | $1 \times 10^{-5}$ | + | 10.6 |

Experimental Example 9

Matrix Production of Rabbit Articular Chondrocytes in the Presence of IL-1

Four NZW line rabbits (Kitayama Labes., Co Ltd.; male; 4-week-old) were sacrificed with bleeding under ether anesthesia and knee joints of femur side were collected aseptically. Only the cortical layer was scrapped with a surgical knife in phosphate buffer (pH 7.2) containing 0.2% glucose and then placed into a 50 ml tube containing phosphate buffered saline containing 0.2% glucose. The collected knee joint cortical layer was cut into as small sections as possible on a dish with a razor, combined with 50 ml of phosphate buffer (100 mg trypsin, 40 mg EDTA·4 Na; pH 7.2) containing 0.2% glucose, supplied with 10× trypsin-ethylenediamine tetraacetic acid tetra sodium salt (EDTA·4Na: GIBCO; Cat. No. 15400-054) and shaken at 37° C. for 15 minutes.

After shaking, the precipitates were collected by centrifugation (1,400 rpm) and washed twice with 40 ml of phosphate buffer (pH 7.2) with 0.2% glucose.

To the washed precipitates was added 40 ml of α-minimum essential medium (MEM: GIBCO; Cat. No. 12571-063) containing 60 mg of collagenase for cell diffusion (Wako Pure Chemical Industries, Ltd., 034-10533) and antibiotics (200 U/ml penicillin G and 200 μg/ml streptomycin sulfate) (GIBCO; Cat. No. 15140-122), and the mixture was transferred to a 100 ml beaker containing a sterilized stirrer bar.

The incubation was conducted in a $CO_2$ incubator at 37° C. for 30 minutes under stirring with a stirrer bar. Deoxyribonuclease I (Takara Shuzo Co., LTD.; Cat. No. 2210A) was then added at a concentration of 70 U/ml. The cultivation was conducted under the same condition for another 30 minutes. The supernatant of the culture was collected in another vessel and the remaining cartilage slips were then cultured again for about 30 minutes in freshly prepared α-minimum essential medium containing 60 mg of collagenase and 70 U/ml deoxyribonuclease I.

To the previously collected culture supernatant and the last culture, from which cartilage slips had been removed using a 40 μm Cell Strainer (FALCON; Cat. No. 2340), 10 ml of α-minimum essential medium (MEM: GIBCO; Cat. No. 12571-063) containing 10% fetal calf serum (GIBCO Cat. No. 10099-141) and antibiotics (200 U/ml penicillin G and 200 μg/ml streptomycin sulfate) (GIBCO; Cat. No. 15140-122) was added and centrifuged (1,400 rpm, 10 minutes).

The precipitates were washed twice with α-minimum essential medium containing 10% fetal calf serum and antibiotics, suspended with an appropriate volume of the same medium, and seeded into 48-well plates (20,000 cells/well). On the next day, the medium was replaced with the same medium.

(Increase of Matrix Production)

Following the above medium exchange procedures; when cells reached to confluent, the medium of test group was replaced with a medium (including 0.1% dimethylsulfoxide) supplied with 1 ng/ml recombinant human IL-1β (PEPRO TECH; Cat. No. 200-01B) and a test compound. As the medium, α-minimum essential medium containing fetal bovine serum and antibiotics (supra), and also 0.2 mM ascorbic acid was used. On the other hand, in the control group, the medium was replaced with the same medium as the test group except that a test compound was not added.

The day when IL-1β containing medium was added was defined as "day 1" and the cultivation was continued until day 3.

After the cultivation, the supernatant was removed from the culture and cells were fixed by addition of 0.25 ml of 10% neutral buffered formalin solution (Wako Pure Chemical Industries, Ltd., Cat. No. 060-01667).

The fixed cells were washed three times with 1 ml of phosphate buffer (pH 7.2) and stained for 4 hours with 0.1% Alcian blue 8GX (Sigma; A3157)) dissolved in 0.1 M hydrochloric acid, which Alcian blue selectively stains matrix (proteoglycan).

After staining, the cells were washed 3 times with 1 ml of phosphate buffer (pH 7.2). Alcian blue which had stained cartilage matrix was dissolved with 0.25 ml of 6 M aqueous guanidine hydrochloride solution and a portion of which was used to determine the absorbance at 620 nm. The amount of Alcian blue used for staining was calculated from the absorbance, which in turn was used for the estimation of the amount of matrix (proteoglycan). The relative percentage was calculated by assuming the proteoglycan production in control group, wherein a test compound was not added, to be 100%. The results are shown in Table 4.

TABLE 4

| Test Compound | Concentration (M) | IL-1β (1 ng/ml) | Proteoglycan Production (%) |
|---|---|---|---|
| Vehicle | 0 | + | 100 |
| Compound(2) | $1 \times 10^{-6}$ | + | 143 |
| Compound No. 53 | $1 \times 10^{-6}$ | + | 211 |
| Compound No. 56 | $1 \times 10^{-6}$ | + | 168 |
| Compound No. 52 | $1 \times 10^{-6}$ | + | 209 |
| Compound No. 57 | $1 \times 10^{-6}$ | + | 169 |
| Compound(11) | $1 \times 10^{-6}$ | + | 121 |

As shown in the table 4 above, in the presence of IL-1, the test compound having PDE4 inhibitory activity increased the matrix production. It is thought that IL-1 plays a important role in cartilage matrix degradation, because IL-1 is expressed in synovial fluid and cartilage cells of osteoarthrosis patients, and induces the production and synthesis of matrix metalloproteinase (MMP), which is matrix (such as cartilage matrix, proteoglycan) catabolic enzyme (The Journal of Pharmacology and Experimental Therapeutics, vol 277, pp. 1672-1675, 1966; Journal of Biochemistry, vol 123, pp. 431-439, 1998; Arthritis & Rheumatism, vol 44, pp. 585-594, 2001). Therefore, the results described above suggested that a PDE4 inhibitor, which is an active ingredient of the present invention, has inhibitory activity against IL-1-related cartilage matrix degradation.

Experimental Example 10

Regenerative Healing Effects on Gonarthrosis Induced by Partial Excision of Medial Meniscus/Abscission of Bilateral Collateral Ligaments (Acclimation)

Japanese White rabbits (male; 10-week-old; 7 rabbits/group) were housed for 16 days at room temperature (23±2° C.) and 55±15% humidity. During the housing period, the rabbits were free to access commercially available food (Oriental Bio Service; LRC4).

(Healing of Gonarthrosis)

Under ether anesthesia, the right knee joint of each rabbit was excised and ½ portion of medial meniscus was isolated with double-edged small straight scissors. The bilateral collateral ligaments were also cut. After the operation, muscle and epidermal tissues were sutured and sterilized. Two weeks from the operation, under ether anesthesia, each rabbit of the test group (7 rabbits/group) was administered intra-articularly the drug-containing microsphere prepared in Example 7-(1), which contains 1 μg of Compound (2). The rabbit of the control group (7 rabbits/group) received the same amount of drug-free microsphere prepared in Control Example 2. Six weeks after the operation, the above-mentioned drug-containing or -free microsphere was again administered. Ten weeks after the operation, under ether anesthesia, rabbits were sacrificed by laparotomy with bleeding and the tibial proximal end was isolated. The isolated tibial proximal end was treated with India ink and then soaked into 10% neutral buffered formalin solution for fixation.

(Experimental Results)

After wiping off the excess India Ink, the overhead surface image of the formalin-fixed tibial proximal end was imported into an analyzer, Image Analyzer (IMAGING RESEARCH, MICD imaging analyzer), with a stereomicroscope (OLYMPUS OPTICAL Co., Ltd. model SZX12-2111). This analyzer was used to measure the area of medial portion where India ink remains (the degenerated area). The gross medial area was also measured and the percentage (%) (the degenerated area rate) of the degenerated medial area in the gross medial area was calculated. The results are shown in Table 5.

TABLE 5

| Drug | Drug amount | Degenerated Area Rate (%) |
|---|---|---|
| Control | 0 μg | 18.86 ± 2.03 |
| Compound(2) | 1 μg | 10.16 ± 1.35 |

Example 1

(1) To 0.1 g of Compound (1) and 1.9 g of lactic acid-glycolic acid copolymer (lactic acid: glycolic acid=50:50; average molecular weight 20,000; PLGA5020: Wako Pure Chemical Industries, Ltd.) was added 4.0 g of methylene chloride, and the mixture was shaken for 30 minutes thoroughly to form an oil phase (O).

(2) The oil phase was added to 8 ml of 0.5% aqueous solution of polyvinyl alcohol (POVAL PVA-220C: Kuraray Co., Ltd.) and emulsified at 25° C. for 5 minutes with homogenizer (Polytron, Kinematica A.G.) to form (O/W) emulsion, wherein the oil phase is dispersed in the water phase.

(3) The emulsion was added to 1000 ml of distilled water, stirred at 400 rpm with Three-one motor (Shinto Scientific Co., Ltd.) and subjected to in-water drying method at 25° C. for 3 hours to remove methylene chloride.

(4) The resultant microsphere suspension was filtered through 150 μm filter to remove aggregates and filtered under reduced pressure through 20 μm filter to remove the water phase. The resultant microsphere was combined with a little amount of distilled water and lyophilized to give 1.6 g of microsphere.

Ten mg of the resultant microsphere was dissolved in 3 ml of acetonitrile. The solution was combined with 7 ml of 0.5 M aqueous sodium chloride solution, stirred with a' mixer (Touch mixer MT-51: YAMATO Scientific Co., Ltd.) and then centrifuged at 2000 rpm for 5 minutes to separate supernatant. A portion of supernatant was loaded on FL-HPLC (column; Hypersil 5-ODS, diameter: 4 mm, length: 300 mm, GL Sciences, Inc., excitation wavelength: 315 nm, fluorescence wavelength: 465 nm) and the drug concentration in the supernatant was determined by comparing with a standard curve prepared separately with a drug solution. On the basis of the resultant concentration and the volume of supernatant, the drug content in microsphere was estimated as 4.21%.

An adequate amount of resulting microsphere was dispersed in a dilute solution of polyoxyethylene sorbitan fatty-acid ester (Tween 80: Nikko Chemicals Co., Ltd.) The particle distribution was measured with a particle size analyzer SALD-1100 (Shimadzu Corporation), and the average particle size was calculated. The average particle size was 57 μm.

(5) The microsphere obtained in (4) above was added to physiological saline (dispersion medium) containing 0.5% carboxymethyl cellulose sodium (Nichirin Chemical Industries) and 0.1% polyoxyethylene sorbitan fatty acid ester (Tween 80: Nikko Chemicals Co., Ltd.) at final drug concentration of 2.5 mg/ml, and the mixture was stirred with a mixer (Touch mixer MT-51: YAMATO Scientific Co., Ltd.) thoroughly to yield microsphere dispersion.

Example 2

(1) Microsphere (1.6 g) was prepared in a manner similar to that described in Example 1-(1) to (4) except that a mixture of 0.57 g of lactic acid-glycolic acid copolymer (lactic acid: glycolic acid=50:50; average molecular weight 20,000; PLGA5020: Wako Pure Chemical Industries, Ltd.) and 1.33 g of lactic acid polymer (average molecular weight 20,000; PLA0020: Wako Pure Chemical Industries, Ltd.) was used.

The drug content and the average particle size of microsphere were measured in a manner similar to that described in Example 1-(4) and proved to be 3.70% and 47.7 μm, respectively.

(2) The microsphere obtained in (1) above was treated in a manner similar to that described in Example 1-(5) to give microsphere dispersion (drug rate: 2.5 mg/ml).

(3) The microsphere obtained in (1) above was treated in a manner similar to that described in Example 1-(5) to give microsphere dispersion (drug rate: 10.0 mg/ml).

Example 3

(1) Microsphere (1.5 g) was prepared in a manner similar to that described in Example 1-(1) to (4) except that lactic acid polymer (average molecular weight 20,000; PLA0020: Wako Pure Chemical Industries, Ltd.) was used.

The drug content and the average particle size of microsphere were measured in a manner similar to that described in Example 1-(4) and proved to be 3.73% and 52.2 μm, respectively.

(2) The microsphere obtained in (1) above was treated in a manner similar to that described in Example 1-(5) to give microsphere dispersion (drug rate: 2.5 mg/ml).

Example 4

(1) To 0.2 g of Compound (1) and 0.3 g of lactic acid polymer (average molecular weight 20,000; PLA0020: Wako Pure Chemical Industries, Ltd.) was added 1.0 g of methylene chloride, and the mixture was shaken with a mixer (Touch mixer MT-51: YAMATO Scientific Co., Ltd.) thoroughly to form an oil phase (O).

(2) The oil phase was added to 4 ml of 0.25% aqueous solution of methyl cellulose (METOLOSE: Shin-Etsu Chemical Co., Ltd.) and emulsified at 25° C. for 5 minutes with homogenizer (Polytron, Kinematica A.G.) to form (O/W) emulsion, wherein the oil phase is dispersed in the water phase.

(3) The emulsion was added to 400 ml of distilled water, stirred at 400 rpm with Three-one motor (Shinto Scientific Co., Ltd.) and subjected to in-water drying method at 25° C. for 3 hours to remove methylene chloride.

(4) The resultant microsphere suspension was filtered through 150 μm filter to remove aggregates and filtered under reduced pressure through 20 μm filter to remove water phase. The resultant microsphere was combined with a little amount of distilled water and lyophilized to give microsphere. The drug content and the average particle size of microsphere were measured in a manner similar to that described in Example 1-(4) and proved to be 39.6% and 33.4 μm, respectively.

Example 5

(1) To 0.05 g of Compound (1) and 0.45 g of lactic acid-glycolic acid copolymer (lactic acid:glycolic acid=50:50; average molecular weight 20,000; R202H: Boehringer Ingelheim Co., Ltd.) was added 1.0 g of methylene chloride, and the mixture was shaken with a mixer (Touch mixer MT-51: YAMATO Scientific Co., Ltd.) thoroughly to form an oil phase (O).

(2) The oil phase was added to 40 ml of 0.5% aqueous solution of polyvinyl alcohol (GOHSENOL EG-40: The Nippon Synthetic Chemical Industry Co., Ltd.) and emulsified at 25° C. for 4 minutes with homogenizer (Polytron, Kinematica A.G.) to form (O/W) emulsion, wherein the oil phase is dispersed in the water phase.

(3) Emulsion was poured into a cylindrical airtight container (inside diameter: 110 mm; volume 1,000 ml) containing 400 ml of purified water, and methylene chloride was removed from the container by stirring at 25° C. and 400 rpm using 4-bladed propeller (diameter: 50 mm, propeller R type: HEIDON) equipped with Three-one motor (BL-600; HEIDON) while supplying nitrogen gas into hollow fibers of cylinder-type hollow fiber membrane module made of silicone rubber (NAGAYANAGI Co., Ltd.) inserted in the container (gas flow rate is 2 L/minute). This procedure was conducted for 1 hour.

The cylindrical hollow fiber membrane module made of silicone rubber used in this procedure is cylinder type NAGASEP M60-1800 of the following specification.

| | |
|---|---|
| Cylinder diameter | 100 mm |
| Cylinder length | 120 mm × 120 mm |
| Membrane thickness of hollow fiber membrane | 60 μm |

| Inside diameter of hollow fiber membrane | 200 μm |
| Outside diameter of hollow fiber membrane | 320 μm |
| Number of hollow fiber | 1800 |
| Effective membrane area of hollow fiber membrane | 0.15 m² |

(4) The resulting microsphere suspension was filtered through 150 μm filter to remove aggregates and filtered under reduced pressure through 20 μm filter to remove water phase. The resultant microsphere was combined with a little amount of distilled water and lyophilized to give 0.26 g of microsphere. The drug content and the average particle size of microsphere were measured in a manner similar to that described in Example 1-(4) and proved to be 3.07% and 71.7 μm, respectively.

Example 6

(1) To 0.05 g of Compound (2) and 0.45 g of lactic acid-glycolic acid copolymer (lactic acid:glycolic acid=50:50; average molecular weight 20,000; RG502H: Boehringer Ingelheim Co., Ltd.), 2.5 g of methylene chloride was added and shaken with a mixer (Touch mixer MT-51: YAMATO Scientific Co., Ltd.) thoroughly to form an oil phase (O).

(2) The oil phase was added to 3 ml of 0.5% aqueous solution of polyvinyl alcohol (POVAL PVA-220C: Kuraray Co., Ltd.) and emulsified at 22° C. for 5 minutes with homogenizer (Polytron: Kinematica A.G.) to form (O/W) emulsion, wherein the oil phase was dispersed in the water phase.

(3) The above procedures (1) and (2) were repeated five times. The resultant emulsions (from 5 trials) were combined, added to 1000 ml of distilled water, and stirred at 400 rpm with Three-one motor (Shinto Scientific Co., Ltd.) to remove methylene chloride by conducting in-water-drying at 25° C. for 1.5 hours, at 40° C. for 1 hour and at 25° C. for 0.5 hours.

(4) The resultant microsphere suspension was filtered through 150 μm filter to remove aggregates and filtered under reduced pressure through 20 μm filter to remove water phase. The resultant microsphere was combined with a little amount of distilled water and lyophilized to give 2.3 g of microsphere.

Ten mg of the resultant microsphere was dissolved in 3 ml of acetonitrile. The solution was combined with 6 ml of aqueous 0.5 M sodium chloride solution, stirred with a mixer (Touch mixer MT-51: YAMATO Scientific Co., Ltd.) and then centrifuged at 2000 rpm for 5 minutes to separate supernatant. A portion of supernatant was loaded on UV-HPLC (column; Hypersil 5-ODS, diameter: 4 mm, length: 300 mm, GL Sciences, Inc., detection wavelength: 240 nm) and the drug concentration in the supernatant was determined by comparing with a standard curve prepared separately with a drug solution. On the basis of the resultant concentration and the volume of supernatant, the drug content in microsphere was estimated. Further, the average particle size was measured in a manner similar to that described in Example 1-(4). As a result, the drug content was 9.9% and the average particle size was 26.4 μm.

(5) The microsphere obtained in (4) above was treated in a manner similar to that described in Example 1-(5) to give microsphere dispersion (drug rate: 0.1 mg/ml).

Example 7

(1) Microsphere (2.2 g) was prepared in a manner similar to that described in Example 6-(1) to (4) except that lactic acid-glycolic acid copolymer (lactic acid:glycolic acid=75:25; average molecular weight 20,000; PLGA7520: Wako Pure Chemical Industries, Ltd.) was used and that 2.0 g of methylene chloride was added.

The drug content and the average particle size of microsphere were measured in a manner similar to that described in Example 6-(4) and proved to be 10.1% and 27.0 μm, respectively.

(2) The microsphere obtained in (1) above was treated in a manner similar to that described in Example 6-(5) to give microsphere dispersion (drug rate: 0.1 mg/ml).

Control Example 1

Control of Example 2

(1) To 0.6 g of lactic acid-glycolic acid copolymer (lactic acid:glycolic acid=50:50; average molecular weight 20,000; PLGA5020: Wako Pure Chemical Industries, Ltd.) and 1.4 g of lactic acid polymer (average molecular weight 20,000) was added 4.0 g of methylene chloride, and the mixture was shaken for 30 minutes thoroughly to form an oil phase (O). In accordance with the procedures described in Example 1-(1) to (4), 1.7 g of microsphere free of drug was obtained.

(2) The microsphere obtained in. (1) above was treated in a same procedures described in Example 1-(5) to prepare microsphere dispersion, wherein the dispersed microsphere concentration in the dispersion is the same as that of Example 2-(3).

Control Example 2

Control of Example 7

To 0.45 g of lactic acid-glycolic acid copolymer (lactic acid:glycolic acid=75:25; average molecular weight 20,000; PLGA7520: Wako Pure Chemical Industries, Ltd.) was added 2.0 g of methylene chloride, and the mixture was shaken with a mixer (Touch mixer MT-51: YAMATO Scientific Co., Ltd.) thoroughly to form an oil phase. In accordance with the procedures described in Example 6-(2) to (4), 2.2 g of microsphere free of drug was obtained.

Test Example 1

To 10 mg of microsphere in a test tube was added 10 ml of phosphate buffer (pH 7.4) containing 0.05% Tween 80, and stirred with a rotating cultivator at 25 rpm in an air-temperature-controlled cabinet at 37° C. When a defined period of time passed from the initiation of stirring, test tube was centrifuged (2000 rpm, 5 min) and of stirring, test tube was centrifuged (2000 rpm, 5 min) and 9 ml of supernatant was sampled and loaded on FL-HPLC (column; Hypersil 5-ODS, diameter: 4 mm, length: 300 mm, GL Sciences, Inc., excitation wavelength: 315 nm, fluorescence wavelength: 465 nm) and the drug content was determined by comparing with a standard curve prepared separately with a drug solution. On the basis of the result and the sampling volume, the elution amount of drug was estimated.

Further, the estimation of elution amount of drug was repeated regularly by adding 9 ml of phosphate buffer (pH 7.4) to the test tube after sampling, and conducting the same procedures under the same conditions, which comprises stirring, sampling, and estimating.

After the final sampling the remaining eluate was removed from the test tube and the drug content in the residual microsphere was determined according to the method described in Example 1-(4).

Figure 5:
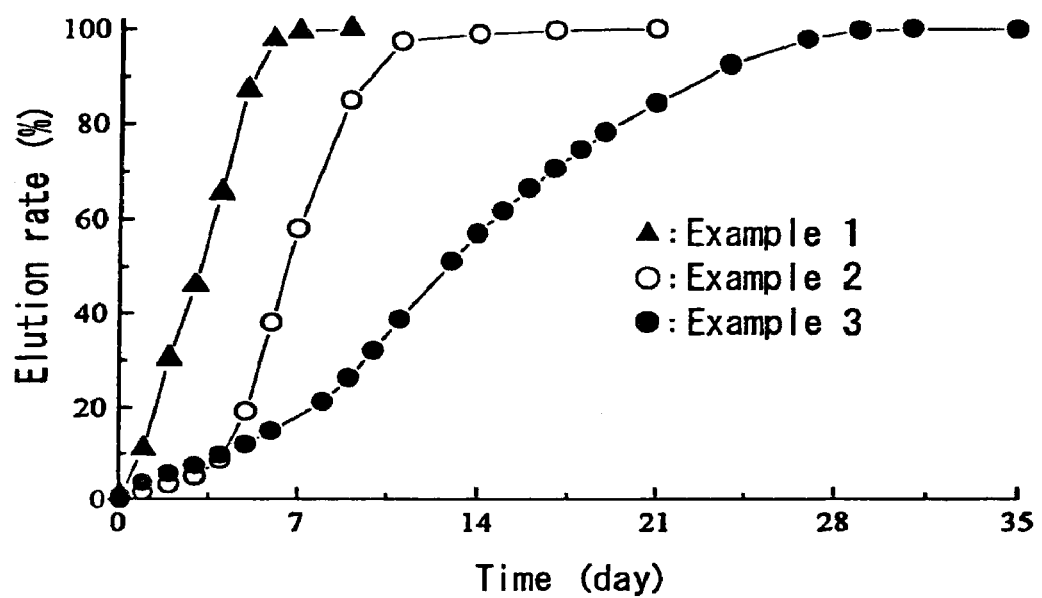
FIG. 5 is a graph showing the in vitro drug elution characteristics of microspheres obtained in Examples 1, 2 and 3.

The above procedures were carried out on the microspheres obtained in Examples 1 to 3. The results are shown in FIG. 5.

The elution rate was calculated based on the assumption that the sum of drug eluted from and remained in the microsphere being 100%.

Test Example 2

Male SD rats (7-weeks-old, 3 rats/group, Japan SLC) were conditioned for a week by housing at room temperature (23±2° C.) under 12 hours light-dark cycle while feeding with food and water ad libitum. Each rat then received rapid-injection of Compound (1) (1 mg/ml) dissolved in physiological saline containing 10% polyethylene glycol 400 ((Wako Pure Chemical Industries, Ltd.) from femoral vein at 0.5 ml/animal (total drug dosage: 0.5 mg/rat).

Figure 6:
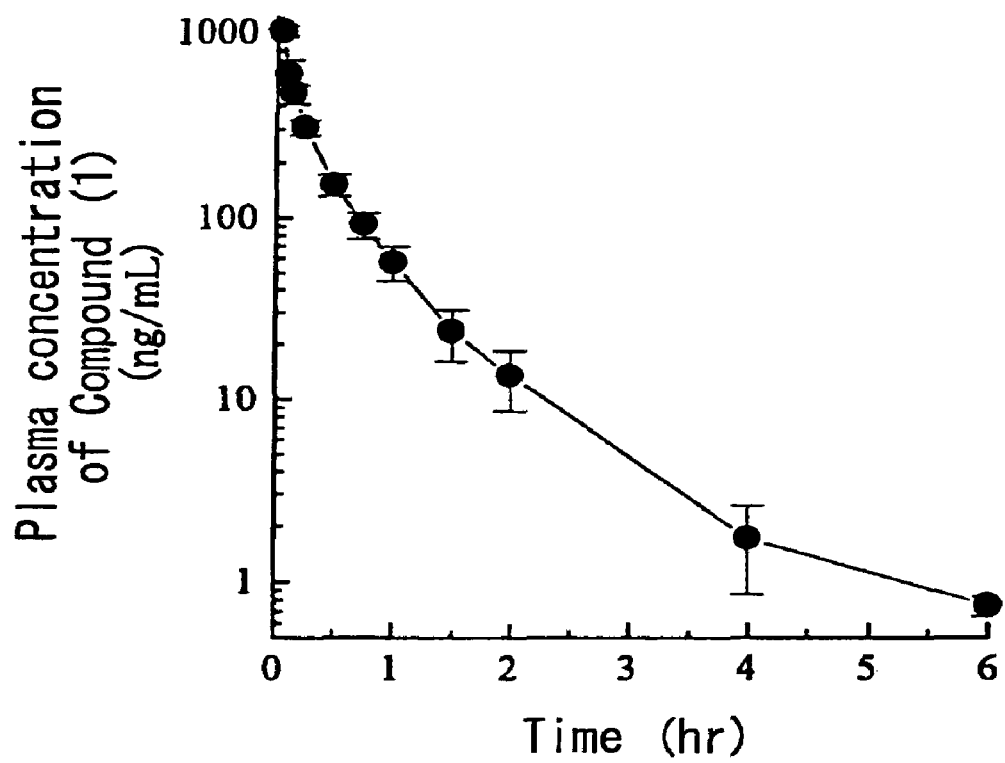
FIG. 6 is a graph showing the time-course of plasma concentration of Compound (1) administered to a rat intravenously. Data are shown by mean±standard deviation (n=3).

After drug administration, under ether anesthesia blood samples were collected at regular time intervals from jugular vein with a syringe containing heparin and centrifuged to obtain plasma samples. To 0.1 ml of plasma were added 0.2 ml of internal standard solution and 1 M dibasic potassium phosphate and then 7.0 ml of chloroform. The mixture was shaken for 10 minutes and centrifuged for 5 minutes to separate 5 ml of organic phase. The resultant organic phase was evaporated to dryness at 40° C. under nitrogen atmosphere, re-dissolved in 0.5 ml of mobile phase and then loaded on FL-HPLC (column; Hypersil 5-ODS, diameter: 4 mm, length: 300 mm, GL Sciences, excitation wavelength: 315 nm, fluorescence wavelength: 465 nm) to determine the plasma concentration. The results are shown in FIG. 6.

Test Example 3

Figure 7:
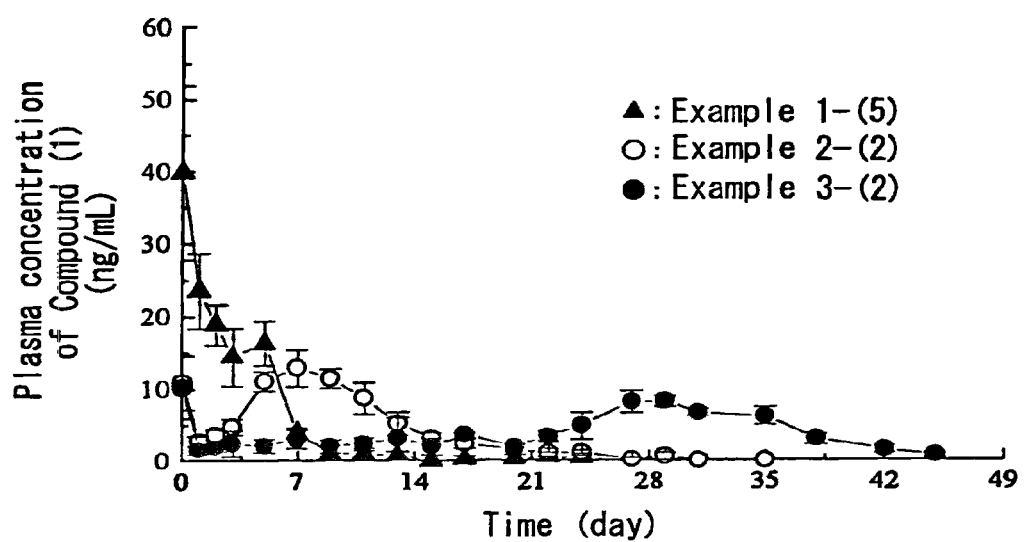
FIG. 7 is a graph showing the time-course of plasma concentration of an active ingredient following the subcutaneous injection of microsphere dispersion obtained in Example 1-(5), 2-(2) or 3-(2) into a rat. Data are shown by mean±standard deviation (n=5).

Male SD rats (7-weeks-old, 5 rats/group, Japan SLC) were conditioned for a week by housing at room temperature (23±2° C.) under 12 hours light-dark cycle while feeding with food and water ad libitum. Each rat then received subcutaneously microsphere dispersion obtained in Examples 1-(5), 2-(2) or 3-(2) from back at 2 ml per rat (total drug dosage: 5 mg/rat). After drug administration, under ether anesthesia, blood samples were collected at regular time intervals from jugular vein with a syringe containing heparin and centrifuged to obtain plasma samples. The concentration of the compound in plasma was determined in a manner similar to that described in Test Example 2. As a result of formulating PDE4 inhibitor into microsphere, the maximum plasma concentration of PDE4 inhibitor could be reduced to 1/25 to 1/100, even when compared with that achieved by intravenous injection of saline containing only a tenth amount of PDE4 inhibitor (Test Example 2). The results are shown in FIG. 7.

Test Example 4

Male SD rats (7-weeks-old, 5 rat per group, Japan SLC) were conditioned for a week by housing at room temperature (23±2° C.) under 12 hours light-dark cycle while feeding with food and water ad libitum. Each rat then received subcutaneously microsphere dispersion obtained in Example 2-(2) from back at 2 ml per rat (total drug dosage: 5 mg/rat).

Figure 8:
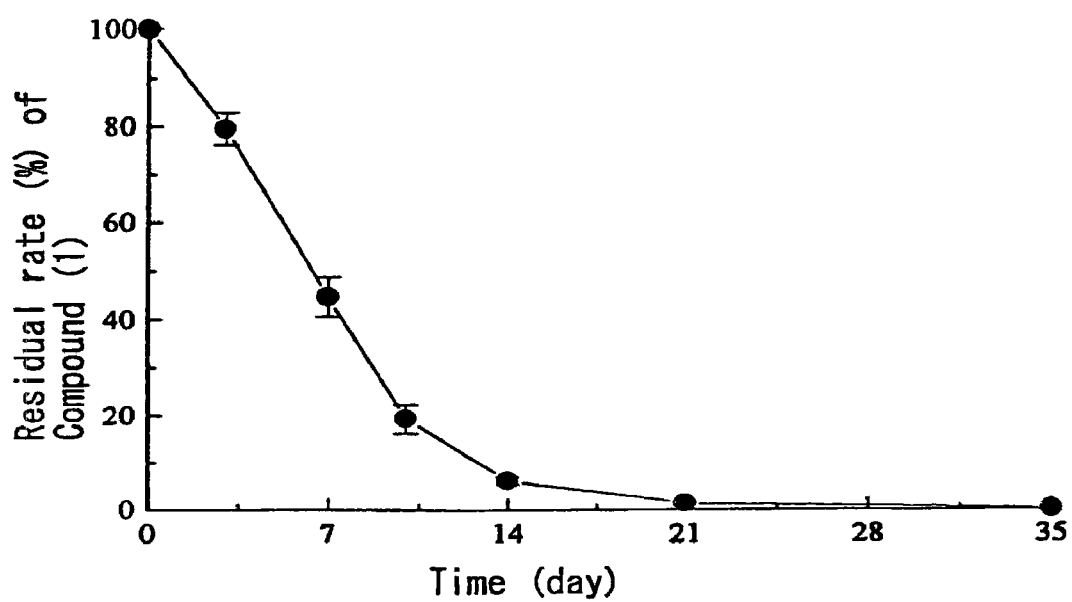
FIG. 8 is a graph showing the time-course of Compound (1) remaining in the preparation following the subcutaneous injection of microsphere dispersion obtained in Example 2-(2) into a rat. Data are shown by mean±standard deviation (n=5).

At days 3, 7, 10, 14, 21 and 35 after drug administration, microspheres were collected from the sites of administration. To the collected microspheres, 5 ml of acetonitrile containing internal control substance was added and dissolved with homogenizer (Polytron: Kinematica A.G.) After centrifugation at 3,000 rpm, 5 minutes, 3 ml of supernatant was collected, combined with 7 ml of 0.5 M aqueous sodium chloride solution, stirred with a mixer (Touch mixer MT-51: YAMATO Scientific Co., Ltd.) and then centrifuged at 2,000 rpm for 5 minutes to separate supernatant. A portion of supernatant was filtrated through KC prep-omni 13 (Katayama Chemistry Inc.) and loaded on FL-HPLC (column; Hypersil 5-ODS, diameter: 4 mm, length: 300 mm, GL Sciences, Inc., excitation wavelength: 315 nm, fluorescence wavelength: 465 nm). The drug concentration was determined by comparing with a standard curve prepared separately with a drug solution. On the basis of the resultant concentration and the volume of supernatant, the residual rate of a drug remaining in microsphere was calculated. The results are shown in FIG. 8.

Test Example 5

Male SD rats (7-weeks-old, Japan SLC) were conditioned for a week by housing at room temperature (23±2° C.) under 12 hours light-dark cycle while feeding with food and water ad libitum. Each rat then received subcutaneously Compound (2)-containing microsphere dispersions obtained in Examples 6-(5) and 7-(2) at 1 ml per rat (total drug dosage: 0.1 mg/rat) from back.

Figure 9:
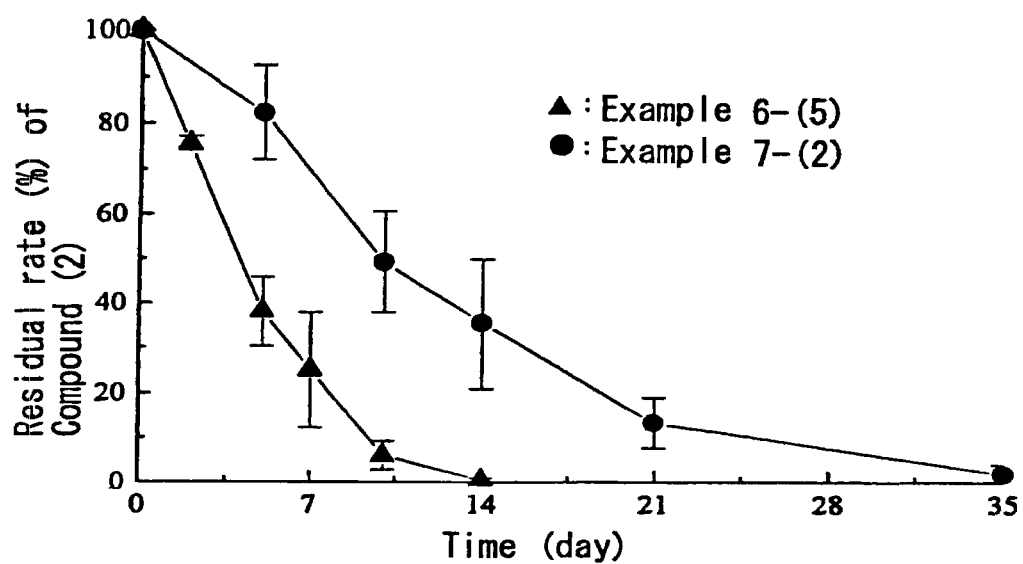
FIG. 9 is a graph showing the time-course of Compound (2) remaining in the preparation following the subcutaneous injection of microsphere dispersion obtained in Example 6-(5) or 7-(2) into a rat. Data are shown by mean±standard deviation (n=4).

Microspheres were collected at regular time intervals from the administration site. To the collected microspheres, 10 ml of acetonitrile was added and dissolved with homogenizer (Polytron: Kinematica A.G.) After centrifugation at 3,000 rpm for 5 minutes, 3 ml of supernatant was collected, combined with 6 ml of 0.5 M aqueous sodium chloride, stirred with a mixer (Touch mixer MT-51: YAMATO Scientific Co., Ltd.) and then-centrifuged at 2000 rpm for 5 minutes to separate supernatant. A portion of supernatant was filtrated through KC prep-omni 13 (Katayama Chemistry Inc.) and loaded on UV-HPLC (column; Hypersil 5-ODS, diameter: 4 mm, length: 300 mm, GL Sciences, Inc., detection wavelength: 240 nm). The drug concentration was determined by comparing with a standard curve prepared separately with a drug solution. On the basis of the resultant concentration and the volume of supernatant, the residual rate of a drug remaining in microsphere was calculated. The results are shown in FIG. 9.

INDUSTRIAL APPLICABILITY

Although only conservative treatment has been considered to be available as drug treatment of cartilage disease, the present composition for regenerative treatment of cartilage disease, which comprises a PDE4 inhibitor as an active ingredient, especially when administered locally to the affected cartilage region, makes it possible to regenerate the cartilage without producing side effects due to systemic action of PDE4 inhibitor, whereby exerts regenerative therapeutic effects on cartilage diseases especially osteoarthrosis. Still higher effect can be achieved by formulating a composition containing a PDE4 inhibitor and a biocompatible and biodegradable polymer into a depot preparation, especially into an injectable microsphere preparation, administering the same locally to an affected cartilage region thereby allowing efficacy to last.

The invention claimed is:

1. A method for regenerative treatment of cartilage disease in a patient, which comprises local administration to an affected cartilage region of a composition comprising a PDE (phosphodiesterase) 4 inhibitor having the following partial structure as an active ingredient:

(A) naphthalene; or
(B) 3-cyclopentyloxy-4-methoxyphenyl.

2. The method according to claim 1, wherein the PDE4 inhibitor is a compound selected from the group consisting of
Compound (1)
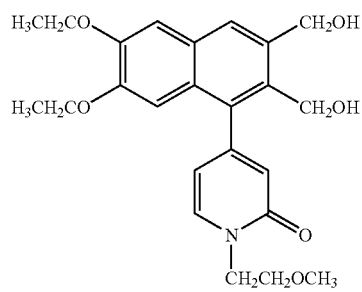
Compound (2)
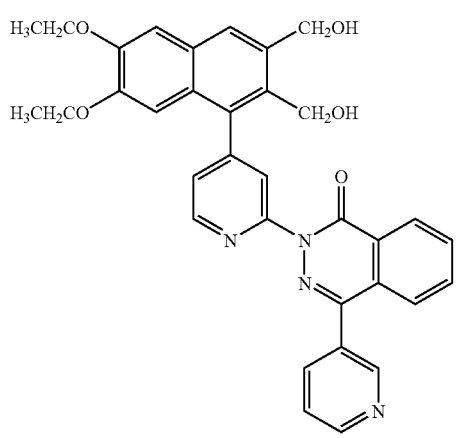
Compound (9)
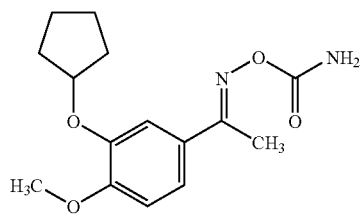
Compound (11)
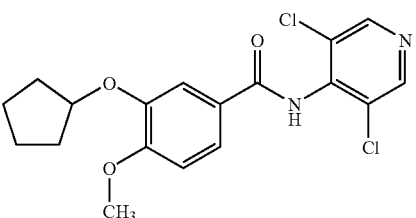
Compound (21)
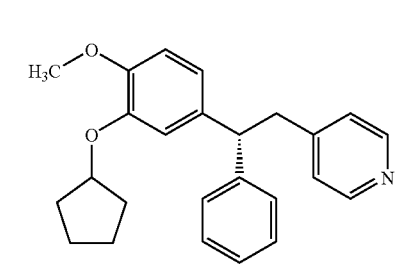
-continued
Compound (27)
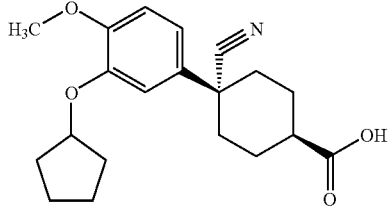
Compound (44)
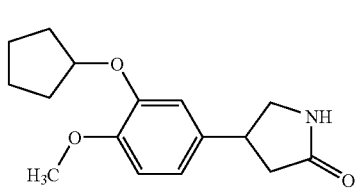
Compound (52)
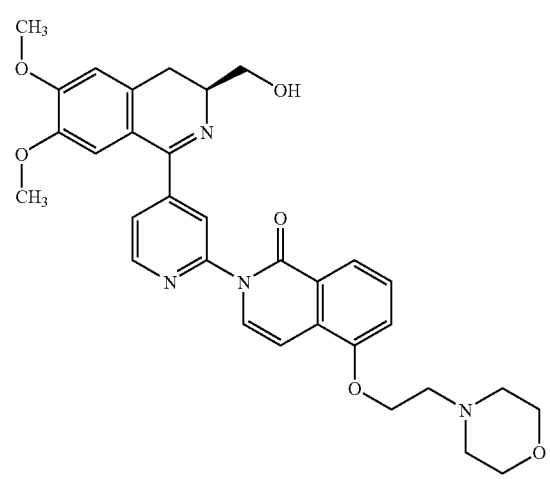
Compound (53)
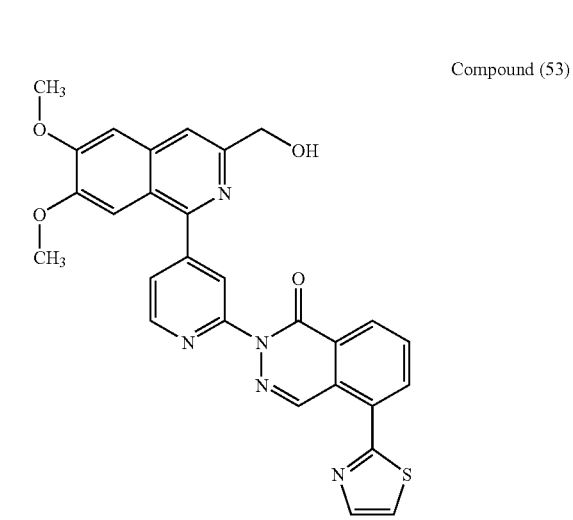

Compound (56)

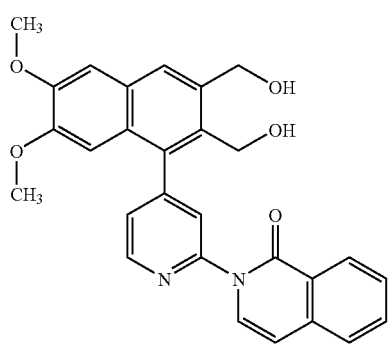

Compound (2)

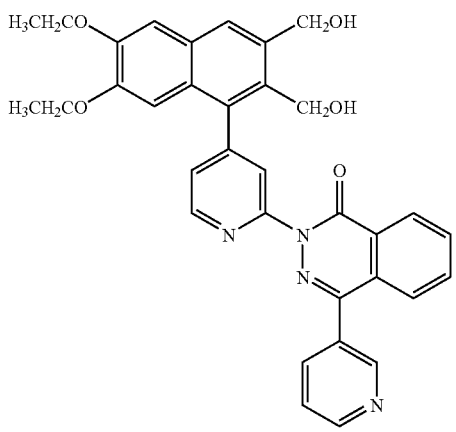

Compound (57)

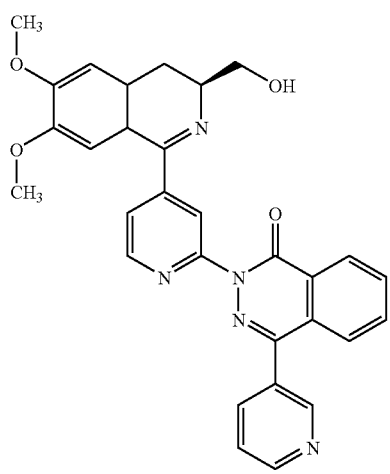

or a pharmaceutically acceptable salt thereof.

3. The method according to claim 1, wherein the PDE4 inhibitor is a compound, which has PDE4 inhibitory activity, having a partial structure of naphthalene or isoquinoline skeleton or a pharmaceutically acceptable salt thereof.

4. The method according to claim 3, wherein the PDE4 inhibitor is a compound selected from the group consisting of Compound (1)

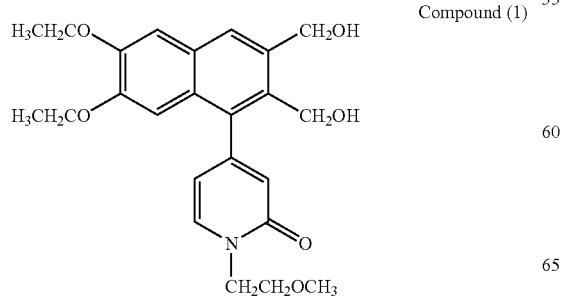

Compound (52)

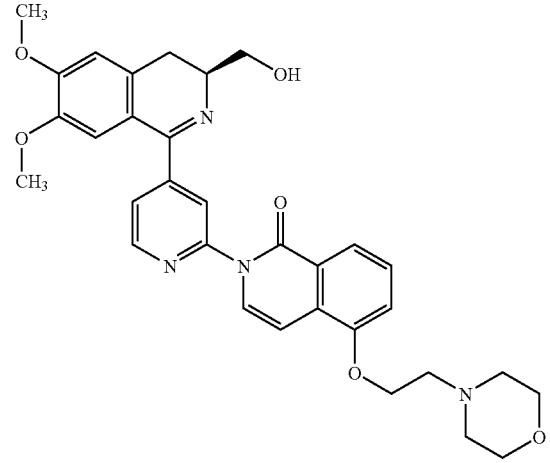

Compound (53)

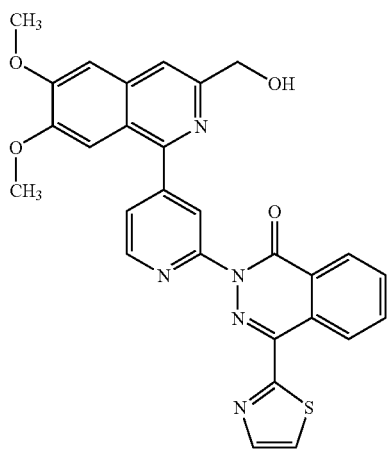

or a pharmaceutically acceptable salt thereof.

5. The method according to claim 4, wherein the PDE4 inhibitor is a compound selected from the group consisting of

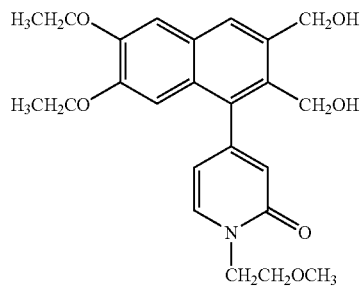
Compond (1)

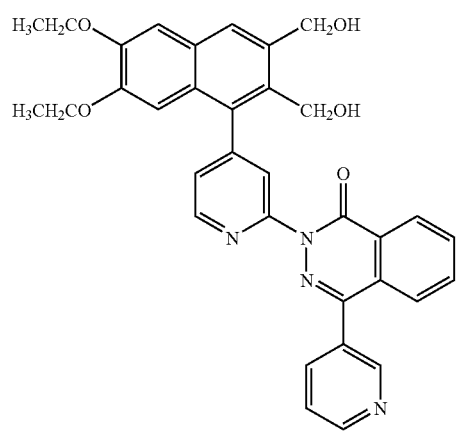
Compound (2)

or a pharmaceutically acceptable salt thereof.

6. The method according to claim 5, wherein the PDE4 inhibitor is

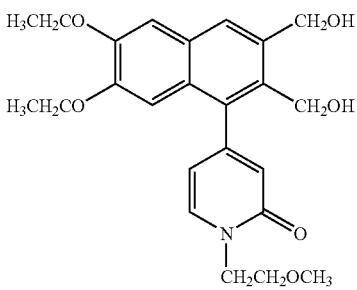
Compound (1)

or a pharmaceutically acceptable salt thereof.

7. The method according to claim 5, wherein the PDE4 inhibitor is

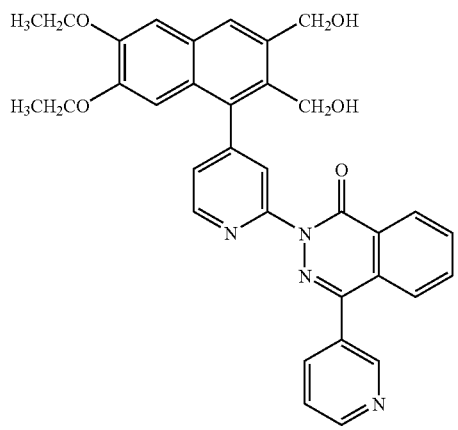
Compound (2)

or a pharmaceutically acceptable salt thereof.

8. The method according to claim 1, wherein $IC_{50}$ of the PDE4 inhibitor is less than 100 nM.

9. The method according to claim 1, which is for regenerative treatment of osteoarthrosis.

10. The method according to claim 1, wherein the composition further comprises a biocompatible and biodegradable polymer for gradually releasing the PDE4 inhibitor at the affected region.

11. The method according to claim 10, wherein the biocompatible and biodegradable polymer is water-insoluble.

12. The method according to claim 11, wherein the composition comprises a microsphere preparation.

13. The method according to claim 12, wherein the particle size of a microsphere is 0.1-150 μm.

14. The method according to claim 12, wherein the composition is an injectable microsphere preparation comprising the microspheres at a concentration of 0.0001-1000 mg/ml in an aqueous solution comprising a dispersant.

15. The method according to claim 14, wherein the injectable microsphere preparation comprises the dispersant at a concentration of 0.01-2% by weight.

16. The method according to claim 14, wherein the dispersant is one or more selected from the group consisting of polyoxyethylene sorbitan fatty acid ester, polyethylene castor oil, carboxymethyl cellulose sodium, sodium alginate, dextran and sodium hyaluronate.

17. The method according to claim 10, wherein the PDE4 inhibitor content is 0.0001-80% by weight of the composition.

18. The method according to claim 11, wherein the water-insoluble biocompatible and biodegradable polymer is a hydroxy fatty acid polyester.

19. The method according to claim 18, wherein the water-insoluble biocompatible and biodegradable polymer is one or more polymers selected from the group consisting of polylactic acid, lactic acid-glycolic acid copolymer and 2-hydroxybutyric acid-glycolic acid copolymer.

20. The method according to claim 18, wherein the water-insoluble biocompatible and biodegradable polymer has an average molecular weight of 2,000-800,000.

* * * * *

UNITED STATES PATENT AND TRADEMARK OFFICE
CERTIFICATE OF CORRECTION

PATENT NO. : 8,399,466 B2
APPLICATION NO. : 12/782514
DATED : March 19, 2013
INVENTOR(S) : Masaharu Takigawa et al.

It is certified that error appears in the above-identified patent and that said Letters Patent is hereby corrected as shown below:

In the Claims

In claim 4, column 44, insert the omitted compounds --

Compound (56)

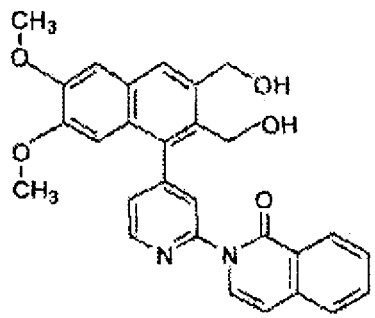

, and

Compound (57)

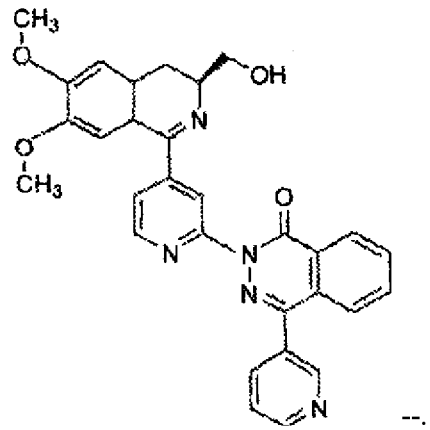

--.

Signed and Sealed this
Fifteenth Day of July, 2014

Michelle K. Lee
*Deputy Director of the United States Patent and Trademark Office*

CERTIFICATE OF CORRECTION (continued)
U.S. Pat. No. 8,399,466 B2

In claim 4, column 44, insert the omitted compounds --

Compound (56)

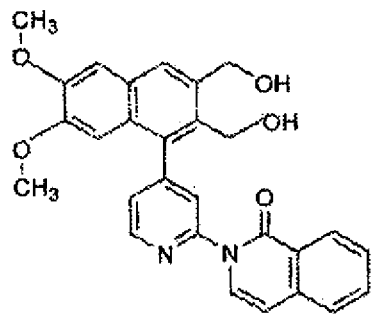

, and

Compound (57)

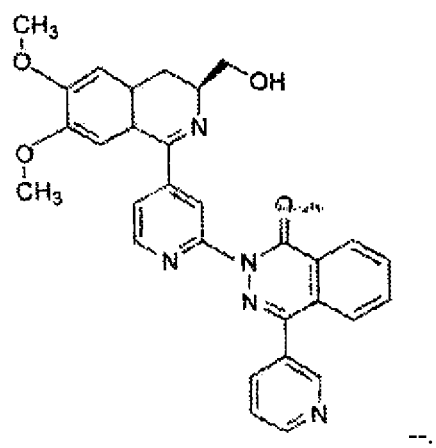

--.